US012758744B2

(12) United States Patent
Ramanathan et al.

(10) Patent No.: US 12,758,744 B2
(45) Date of Patent: Oct. 13, 2026

(54) CATHETER DEVICE

(71) Applicant: ProMedica Health System, Inc., Toledo, OH (US)

(72) Inventors: P. Kasi Ramanathan, Toledo, OH (US); Eugene J. Jung, Toledo, OH (US); Diane M. Chelsea, Toledo, OH (US)

(73) Assignee: PROMEDICA HEALTH SYSTEM, INC., Toledo, OH (US)

( * ) Notice: Subject to any disclaimer, the term of this patent is extended or adjusted under 35 U.S.C. 154(b) by 873 days.

(21) Appl. No.: 18/171,234

(22) Filed: Feb. 17, 2023

(65) Prior Publication Data

US 2023/0201531 A1 Jun. 29, 2023

(51) Int. Cl.

| | |
|---|---|
| ***A61M 25/01*** | (2006.01) |
| ***A61M 25/00*** | (2006.01) |
| ***A61M 25/06*** | (2006.01) |

(52) U.S. Cl.

CPC . *A61M 25/0102* (2013.01); *A61M 2025/0047* (2013.01); *A61M 25/0053* (2013.01); *A61M 25/0068* (2013.01); *A61M 2025/0175* (2013.01)

(58) Field of Classification Search

CPC .......... A61M 25/0053; A61M 25/0054; A61M 25/0068; A61M 25/0662; A61M 25/0152;

(Continued)

(56) References Cited

U.S. PATENT DOCUMENTS

| | | | | |
|---|---|---|---|---|
| 3,503,385 A * | 3/1970 | Stevens | ............. | A61M 25/0147 604/95.01 |
| 5,207,648 A * | 5/1993 | Gross | ................ | A61M 25/0014 604/523 |

(Continued)

FOREIGN PATENT DOCUMENTS

| | | |
|---|---|---|
| CN | 1105843 A | 8/1995 |
| CN | 102497906 A | 6/2012 |

(Continued)

OTHER PUBLICATIONS

Saeko Takahashi, Shigeru Saito, Shinji Tanaka, Yusuke Miyashita, Takaaki Shiono, Fumio Arai, Hiroshi Domae, Shutaro Satake, and Takenari Itoh; New Method to Increase a Backup Support of a 6 French Guiding Coronary Catheter; Catheterization and Cardiovascular Interventions; 2004, pp. 452-456, vol. 62.

*Primary Examiner* — Chelsea E Stinson
*Assistant Examiner* — Hamza A Darb
(74) *Attorney, Agent, or Firm* — Michael E. Dockins; Shumaker, Loop & Kendrick, LLP

(57) ABSTRACT

A catheter device includes a housing extending from a proximal end to a distal end, a fixed tubular segment extending from a proximal end immovably coupled to the housing to a distal end, an outer tubular member extending from a proximal end immovably coupled to the housing to a distal end, and an inner tubular member extending from a proximal end to a distal end. The inner tubular member is slidably received within an interior of the outer tubular member and is slidably received over an exterior of the fixed tubular segment. The inner tubular member is configured to slide relative to each of the fixed tubular segment and the outer tubular member to selectively extend or retract the distal end of the inner tubular member relative to the distal end of the outer tubular member.

20 Claims, 15 Drawing Sheets

(58) Field of Classification Search
CPC .. A61M 2025/0047; A61M 2025/1081; A61M 2025/0175; A61M 2025/0004
See application file for complete search history.

(56) References Cited

U.S. PATENT DOCUMENTS

| | | | | |
|---|---|---|---|---|
| 5,396,880 | A | 3/1995 | Kagan et al. | |
| 5,472,017 | A | 12/1995 | Kovalcheck | |
| 5,507,768 | A * | 4/1996 | Lau | A61F 2/97 606/198 |
| 5,545,138 | A * | 8/1996 | Fugoso | A61M 25/104 604/524 |
| 5,769,885 | A * | 6/1998 | Quiachon | A61F 2/954 128/898 |
| 6,090,072 | A | 7/2000 | Kratoska et al. | |
| 7,717,899 | B2 | 5/2010 | Bowe et al. | |
| 8,401,673 | B2 | 3/2013 | Bowe et al. | |
| 8,556,850 | B2 * | 10/2013 | Tegg | A61M 25/0147 604/95.04 |
| RE45,776 | E | 10/2015 | Root et al. | |
| 9,247,990 | B2 | 2/2016 | Kauphusman et al. | |
| 9,795,408 | B2 * | 10/2017 | Chin | A61M 25/0119 |
| 10,668,258 | B1 | 6/2020 | Calhoun et al. | |
| 11,612,720 | B2 * | 3/2023 | Pittman | A61M 25/0136 604/95.04 |
| 2001/0027310 | A1 * | 10/2001 | Parisi | A61L 31/12 604/524 |
| 2003/0130713 | A1 * | 7/2003 | Stewart | A61B 17/00234 607/119 |
| 2004/0044350 | A1 | 3/2004 | Martin et al. | |
| 2004/0097819 | A1 | 5/2004 | Duarte | |
| 2005/0004553 | A1 * | 1/2005 | Douk | A61M 25/0021 604/523 |
| 2005/0027236 | A1 * | 2/2005 | Douk | A61M 1/84 604/40 |
| 2005/0027345 | A1 | 2/2005 | Horan et al. | |
| 2005/0070844 | A1 | 3/2005 | Chow et al. | |
| 2005/0075661 | A1 | 4/2005 | Levine et al. | |
| 2005/0090890 | A1 | 4/2005 | Wu et al. | |
| 2008/0172036 | A1 | 7/2008 | Stys | |
| 2009/0024084 | A1 * | 1/2009 | Khosla | A61M 25/0097 604/95.01 |
| 2009/0270835 | A1 | 10/2009 | Kushner | |
| 2010/0160858 | A1 | 6/2010 | Fischer et al. | |
| 2010/0217234 | A1 * | 8/2010 | Grovender | A61M 25/0015 156/308.2 |
| 2010/0280449 | A1 | 11/2010 | Alvarez et al. | |
| 2011/0015728 | A1 | 1/2011 | Jimenez et al. | |
| 2011/0034764 | A1 | 2/2011 | Verbeek | |
| 2011/0065990 | A1 | 3/2011 | Verbeek | |
| 2011/0077621 | A1 | 3/2011 | Graham et al. | |
| 2011/0092956 | A1 * | 4/2011 | Soer | A61B 1/00156 604/528 |
| 2012/0016307 | A1 * | 1/2012 | Burkholz | A61B 5/150916 604/168.01 |
| 2012/0029334 | A1 | 2/2012 | Tegg | |
| 2012/0109079 | A1 | 5/2012 | Asleson et al. | |
| 2013/0131591 | A1 | 5/2013 | Berthiaume et al. | |
| 2014/0018732 | A1 * | 1/2014 | Bagaoisan | A61M 25/0136 604/95.04 |
| 2014/0052208 | A1 | 2/2014 | Ransbury et al. | |
| 2014/0180127 | A1 * | 6/2014 | Meyer | A61B 8/445 600/407 |
| 2014/0277564 | A1 | 9/2014 | Windheuser et al. | |
| 2015/0119853 | A1 | 4/2015 | Gainor et al. | |
| 2015/0173782 | A1 | 6/2015 | Garrison et al. | |
| 2015/0223955 | A1 | 8/2015 | Li et al. | |
| 2016/0228682 | A1 | 8/2016 | Graham et al. | |
| 2016/0367787 | A1 | 12/2016 | Van Hoven et al. | |
| 2017/0043066 | A1 | 2/2017 | Laub | |
| 2017/0238953 | A1 * | 8/2017 | Yang | A61B 17/22031 |
| 2017/0258614 | A1 | 9/2017 | Griffin | |
| 2017/0274180 | A1 * | 9/2017 | Garrison | A61M 25/0054 |
| 2017/0291008 | A1 | 10/2017 | Hillukka et al. | |
| 2018/0200490 | A1 * | 7/2018 | Gianotti | A61M 29/00 |
| 2018/0242962 | A1 | 8/2018 | Walen et al. | |
| 2018/0256848 | A1 | 9/2018 | Ramanathan | |
| 2019/0000429 | A1 * | 1/2019 | Magana | A61M 25/0113 |
| 2019/0143078 | A1 * | 5/2019 | Tierney | A61M 25/0113 604/544 |
| 2019/0192176 | A1 | 6/2019 | Palushi et al. | |
| 2019/0290314 | A1 | 9/2019 | Gemer et al. | |
| 2019/0351182 | A1 | 11/2019 | Chou et al. | |
| 2019/0366036 | A1 * | 12/2019 | Jalgaonkar | A61M 25/008 |
| 2019/0388649 | A1 * | 12/2019 | Watson | A61M 25/0041 |
| 2020/0008820 | A1 | 1/2020 | Aboytes et al. | |
| 2020/0061340 | A1 | 2/2020 | Mixter et al. | |
| 2020/0086085 | A1 * | 3/2020 | Sarradon | A61M 25/007 |
| 2020/0121166 | A1 | 4/2020 | Thissen | |
| 2021/0106788 | A1 * | 4/2021 | Brown | A61M 25/06 |
| 2021/0212707 | A1 | 7/2021 | Chou et al. | |
| 2021/0290897 | A1 * | 9/2021 | Burkholz | A61M 39/02 |
| 2021/0290906 | A1 * | 9/2021 | Burkholz | A61M 25/0122 |
| 2021/0290914 | A1 * | 9/2021 | Burkholz | A61M 25/09 |
| 2021/0298730 | A1 * | 9/2021 | Baxter | A61M 25/0054 |
| 2021/0338983 | A1 | 11/2021 | Zhang et al. | |
| 2021/0338984 | A1 * | 11/2021 | Booker | A61M 25/0097 |
| 2021/0379333 | A1 | 12/2021 | Ramanathan et al. | |
| 2022/0008692 | A1 * | 1/2022 | Pulugurtha | A61M 25/0054 |
| 2022/0370761 | A1 * | 11/2022 | Chou | A61M 25/04 |
| 2023/0135731 | A1 * | 5/2023 | Farrar | A61B 5/150732 600/581 |
| 2023/0363787 | A1 * | 11/2023 | Liu | A61M 25/1006 |
| 2024/0065593 | A1 * | 2/2024 | Gatoro | A61M 25/0662 |
| 2024/0075250 | A1 * | 3/2024 | Boud | A61M 25/0606 |

FOREIGN PATENT DOCUMENTS

| | | | | |
|---|---|---|---|---|
| CN | 103945898 | A | 7/2014 | |
| CN | 109715243 | A | 5/2019 | |
| EP | 0505686 | A1 | 9/1992 | |
| WO | WO-2017058818 | A1 * | 4/2017 | A61M 25/0905 |
| WO | 2018023038 | A1 | 2/2018 | |
| WO | 2020247964 | A1 | 12/2020 | |
| WO | WO-2021170267 | A1 * | 9/2021 | A61M 1/3667 |

* cited by examiner

CATHETER DEVICE

FIELD

The present technology relates to catheter devices, including guide extension catheters that provide improved control of distal configurations thereof.

INTRODUCTION

This section provides background information related to the present disclosure which is not necessarily prior art.

Guide catheters are used in nearly all of the approximately three million Percutaneous Coronary Intervention (PCI) procedures performed each year in the world. Percutaneous coronary intervention procedures are intended to clear blockages in coronary arteries that nourish the heart with blood. A blocked artery, if severe, can lead to irreversible heart muscle damage, stroke, or death if the blockage is left untreated. A guide catheter is designed to access coronary arteries during PCI so operators can deliver therapeutic devices, such as an angioplasty balloon or coronary stent, to treat the vessel blockage and restore blood flow to the heart. The performance of a guide catheter is critical to the success of a PCI procedure.

A guide catheter, a guidewire, and a stent mounted on a balloon catheter are the mainstays of PCI. While there are other niche devices used, the aforementioned three devices are used in almost every PCI procedure today. Even though tremendous improvements in coronary guidewire and stent design have occurred through the years, advances in guide catheter design have been minimal at best.

At the same time, guide catheters have decreased in diameter from 7 Fr or 8 Fr twenty or so years ago to 5 Fr or 6 Fr today. The smaller diameter helps to reduce complications at the vascular access site, near the groin or in the arm.

However, an unwanted consequence in reducing the guide catheter size is a reduction in support. The term support as used here describes the stability of guide catheter positioning at or near the coronary ostium, for example. It is essential that the guide catheter remains in position so that the guidewire and stent can be delivered to the treatment site. Loss of support describes a situation where the guide catheter backs out of position near the ostium as the operator tries to advance the guidewire or stent to the lesion in the coronary artery, for example. When this occurs, the operator must take his/her attention away from treating the blockage and attempt to restore the guide catheter into proper position near the ostium. Often, guide catheter backout recurs repeatedly during the same procedure, leading to operator frustration and lengthened procedure time. In addition, repeated catheter manipulation at or in the coronary artery can result in an injury to the vessel, which can create an adverse complication to the patient.

The concept of a guide extension catheter, in other words an inner catheter placed concentrically within an outer catheter, to enhance guide catheter support has been previously explored. Takahashi et al. ("New Method to Increase a Backup Support of Six French Guiding Coronary Catheter", Catheterization and Cardiovascular Interventions, 63:452-456, 2004) published data measuring the added support of an inner guide catheter extension within a conventional 6 Fr outer guide catheter. In the Takahashi study, the distal end of the inner catheter was extended past the distal end of the outer catheter into a model of a coronary vessel to evaluate catheter support. The results demonstrated that the above configuration offered improved support, enabling a 5 Fr inner and 6 Fr outer catheter system to exceed the amount of support of a larger guide catheter.

A number of devices in the art more broadly use a 2-in-1 catheter concept for applications beyond guide catheter extension devices. For example, Bowe (U.S. Pat. Nos. 7,717,899B2, 8,401,673B2) teaches of changing the shape of the catheter tip by rotating and translating the inner catheter relative to the outer catheter. In addition, Stys and Gainor (US20080172036A1, US20150119853A1) describe 2-in-1 catheters that can change shape and tip stiffness by manipulating the rotational and axial positions of one of the catheters relative to the other. However, having two separate, non-integrated catheters necessitate a cumbersome process in use.

Another 2-in-1 catheter concept by Root et al. (USRE45776E1) utilizes a rapid exchange style construction utilizing a pushrod attached to a short tubular member. Such devices extend into coronary arteries beyond the distal end of the guide catheter to enhance support. However, the use of guide catheter extension devices introduces an additional device into the procedure, adds significant cost, and adds to procedure time. In addition, separate extension devices take up space inside the lumen of the guide catheter reducing the space available for other devices. Importantly, as reported in the Manufacturer and User Facility Device Experience (MAUDE) database of the U.S. Food & Drug Administration, extension devices have been reported to cause vessel trauma.

The use of separate guide extension catheters, such as described above, can provide improved guide catheter support. However, such approaches, whether employing full length catheters or shorter rapid exchange devices with a pushrod element, are in essence, makeshift solutions. There accordingly remains a need to improve guide catheter design to overcome poor support while preserving improvements in catheter diameter reduction. Enhancing support, in turn, eliminates or reduces the frequent need to utilize a separate guide extension catheter.

Transcatheter Aortic Valve Replacement (TAVR) procedures could similarly benefit from such a 2-in-1 catheter device in applications beyond those described herein. An integrated guide catheter/guide extension system would offer the same benefits along with improved workflow and a reduced number of devices needed to perform this complex and difficult procedure.

There consequently remains a need to more elegantly integrate guide extension catheters to provide the user with a simpler and easier set of controls to precisely and quickly change the catheter distal configuration. Such devices should more efficiently and cost effectively solve the problem of poor guide catheter support frequently experienced with currently available products and technologies in the art.

SUMMARY

The present technology includes articles of manufacture, systems, and processes that relate to a catheter device, including coronary catheters having integrated guide extension functionalities and improved support characteristics.

Ways of constructing and using catheter devices are provided, where such catheter devices include an outer tubular member, and inner tubular member, and a control mechanism. The outer tubular member has a proximal end and a shaped distal end. The inner tubular member has at least a portion thereof coaxially positioned within the outer tubular member, where the inner tubular member includes a proximal end and a distal end. The control mechanism has a housing with a means to seal an inner luminal space thereof. The control mechanism is coupled to the proximal end of the outer tubular member and the proximal end of the inner tubular member. The control mechanism is configured to extend and retract the distal end of the inner tubular member from the shaped distal end of the outer tubular member. A lumen of the inner tubular member is unobstructed and can accommodate various implements, treatment operations, and delivery of devices therethrough, such as balloons and stents when the inner tubular member is deployed at a desired location within a patient.

According to another embodiment of the present invention, a catheter device comprises a housing extending from a proximal end to a distal end. A fixed tubular segment extends from a proximal end to a distal end with the proximal end of the fixed tubular segment immovably coupled to the housing adjacent the proximal end of the housing. An outer tubular member extends from a proximal end to a distal end with the proximal end of the outer tubular member immovably coupled to the housing adjacent the distal end of the housing. An inner tubular member extends from a proximal end to a distal end with the inner tubular member slidably received within an interior of the outer tubular member and slidably received over an exterior of the fixed tubular segment. The inner tubular member is configured to slide relative to each of the fixed tubular segment and the outer tubular member to selectively extend the distal end of the inner tubular member in a distal direction away from the distal end of the outer tubular member and/or to retract the distal end of the inner tubular member in a proximal direction towards the distal end of the outer tubular member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1A includes an enlarged view of an encircled portion of a coronary vessel of the patient.

FIG. 1B includes an enlarged view of the encircled portion of the coronary vessel showing a progression of an angioplasty balloon, not part of the invention, from an unexpanded state to an expanded state.

DETAILED DESCRIPTION

Figure 1C:
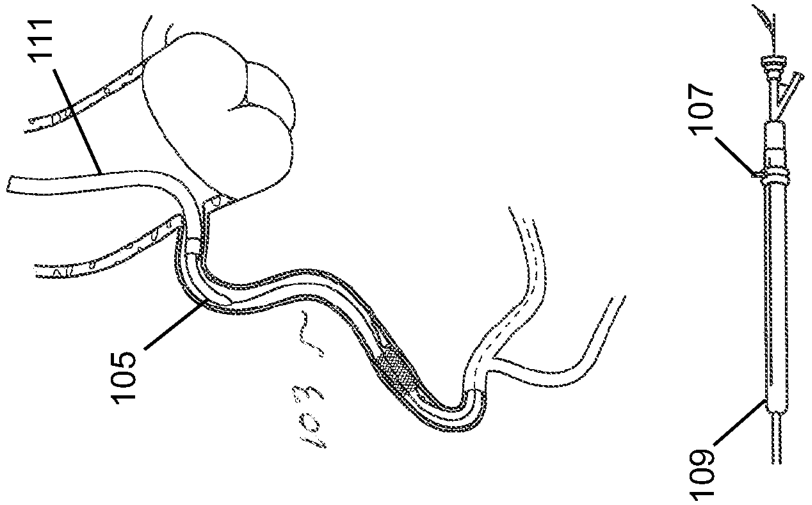
FIG. 1C shows the embodiment of the catheter device according to FIG. 1B, where the inner tubular member is being retracted.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed. “A” and “an” as used herein indicate “at least one” of the item is present; a plurality of such items may be present, when possible. Except where otherwise expressly indicated, all numerical quantities in this description are to be understood as modified by the word “about” and all geometric and spatial descriptors are to be understood as modified by the word “substantially” in describing the broadest scope of the technology. “About” when applied to numerical values indicates that the calculation or the measurement allows some slight imprecision in the value (with some approach to exactness in the value; approximately or reasonably close to the value; nearly). If, for some reason, the imprecision provided by “about” and/or “substantially” is not otherwise understood in the art with this ordinary meaning, then “about” and/or “substantially” as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term “comprising,” as a synonym of non-restrictive terms such as including, containing, or having, is used herein to describe and claim embodiments of the present technology, embodiments may alternatively be described using more limiting terms such as “consisting of” or “consisting essentially of” Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of “from A to B” or “from about A to about B” is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology is drawn to catheter devices and uses thereof that include inner and outer tubular members and a control mechanism. The outer tubular member includes a proximal end and a shaped distal end and the inner tubular member includes a proximal end and a distal end. At least a portion of the inner tubular member is coaxially positioned within the outer tubular member. The control mechanism includes a housing having a means to seal an inner luminal space thereof. The control mechanism is coupled to the proximal end of the outer tubular member and the proximal end of the inner tubular member. The distal end of the inner tubular member can extend and retract from the shaped distal end of the outer tubular member by operation of the control mechanism.

The catheter device improves the state of the art in coronary guide catheters by providing for a low profile diameter, 6 Fr or less, guide catheter designed to offer enhanced support to prevent guide catheter backout or loss of support. In addition, the catheter device is configured to provide the above benefits in a single, convenient and easy to use catheter system based on a novel mechanism contained within or near the proximal end of the catheter. The catheter device offers enhanced workflow benefits, ease of use, and at the same time, eliminates the need for expensive ancillary devices. The extra devices needed in procedures today add clutter to the work space and consume valuable space inside the guide catheter. The space inside the present catheter device can instead be used for other purposes, for example, allowing room for a buddy wire technique.

Certain embodiments of the catheter device include an outer tubular member with a shaped distal end, a straight inner tubular member, and a control mechanism and its housing. The inner and outer tubular members are coaxially arranged with their respective proximal ends coupled to a control mechanism at or near the proximal end of the device. The control mechanism housing has an integrated luer fitting or means to seal the inner luminal space using an ancillary sealing means, such as a Touhy Borst fitting.

The control mechanism can be wholly or partially contained in the control mechanism housing near or at the proximal end of the catheter system. The control mechanism provides a means to extend the inner tubular member from inside the outer tubular member so it extends beyond the distal end of the outer tubular member. The control mechanism is also adapted to retract the inner tubular member so it is fully contained within the outer tubular member. The range of extension and retraction are controlled by stops in the control mechanism and define the maximum extension of the inner tubular member and the full range of travel of the inner tubular member relative to the distal end of the outer tubular member. The control mechanism and all of its parts are configured to be outside the inner tubular member so as to not utilize any space within the catheter system lumen, thus maximizing the available space within the inner lumen for delivering other devices such as guidewires, stent delivery catheters, etc.

The means of extending and controlling the inner tubular member movement include, but are not limited to, manual, mechanical, electrical, electromagnetic and other means to extend the inner tubular member from within the outer tubular member and retract the inner tubular member into the outer tubular member. An example includes a manually operated control mechanism with an integrated luer that incorporates an external control ring and a means to convert rotational movement of the external control ring to a longitudinal movement of the inner tubular member using a mechanical system of a rotating knob, a gear set, pulley(s), and/or pushrod(s), etc. The aforementioned control mechanism is coupled to the inner tubular member thus translating movement of the external control ring to extend the inner tubular member from the outer tubular member and retract the inner tubular member into the outer tubular member.

The shaped distal end of the outer tubular member can be one of many existing shapes used in guide catheters. An example can be a Judkins right curve or an Amplatzer left curve or any of the standard Judkins or Amplatzer curves widely available. These and other curved shaped distal ends were developed to gain easier access to a specific coronary artery and to provide support for the catheter to remain in position during the procedure.

The outer tubular member is immovably affixed to the control mechanism and/or hub and the luminal space is sealed to prevent blood loss or air ingress/egress. A hub is an interface fitting designed to attach an accessory to the catheter in a sealed manner that prevents air leaks. The inner tubular member is coupled to the control mechanism, which, with operator manipulation, can extend the tip of the inner tubular member beyond the distal tip of the outer tubular member.

This catheter device provides the extra support and stability of a larger guide catheter or the combination of a standard guide catheter and guide extension catheter. The mechanical system of a rotating knob, a gear set, pulley(s), and/or pushrod(s), etc mentioned above describes the means of actuating the movement of the inner tubular member. Importantly, the actuation means, which can extend and retract the inner tubular member, acts without utilizing any space inside the inner tubular member inner lumen. Thus, the luminal space is preserved for other uses, such as inserting additional devices into the artery.

In summary, this catheter device offers the benefit of allowing a smaller vascular access site to reduce complications and a control mechanism that can extend the inner tubular member into the vasculature when needed, all in a single, easy to use catheter system. It does this in a novel way minimizing device length, and consequently, preserving the length a device inserted through the catheter device can be advanced into the vasculature. Another benefit is this design reduces clutter at the proximal end, where the operator must manipulate devices such as a guidewire or stent delivery catheter. The present technology can be used in a variety of applications such as interventional cardiology, interventional neurology and peripheral vascular intervention where traversing vasculature, providing guide catheter support, and offering a low device profile are needed.

Example embodiments of the present technology are provided with reference to the several figures enclosed herewith.

Figure 1B:
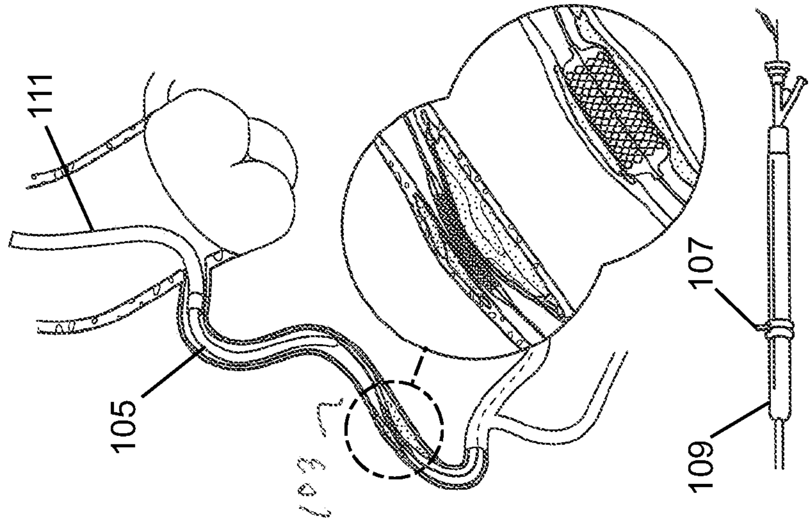
FIG. 1B shows the embodiment of the catheter device according to FIG. 1A, where the inner tubular member is in an extended state.
Figure 1A:
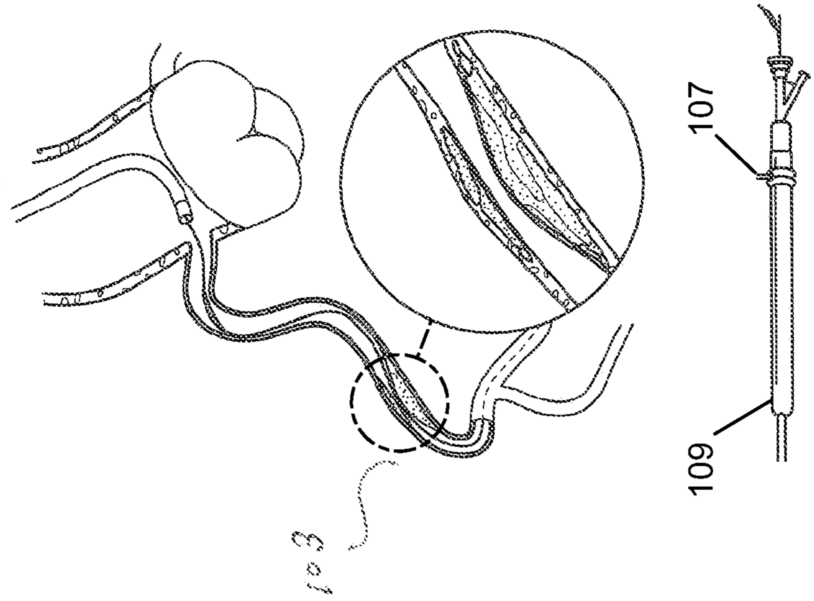
FIG. 1A shows an embodiment of a catheter device according to the present technology positioned within a patient's anatomy, where an inner tubular member is in a retracted state.

One embodiment of a catheter device 101 located in a coronary vessel 103 is shown in FIGS. 1A, 1B, and 1C. The catheter device 101 has an inner tubular member 105 that can be extended into the coronary vessel 103 to enhance guide catheter support, as shown in FIG. 1B. In the lower part of each panel, the position of a slider 107, in a control mechanism 109, corresponds to the position of the inner tubular member 105 with respect to an outer tubular member 111. The slider 107 position and corresponding inner tubular member 105 position are shown in a fully retracted state (FIG. 1A), a fully extended state (FIG. 1B), and an intermediate state (FIG. 1C). At the completion of the procedure, the extended inner tubular member 105 can be retracted and the guide catheter system withdrawn from the anatomy as shown in progress in FIG. 1C.

Figure 2A:
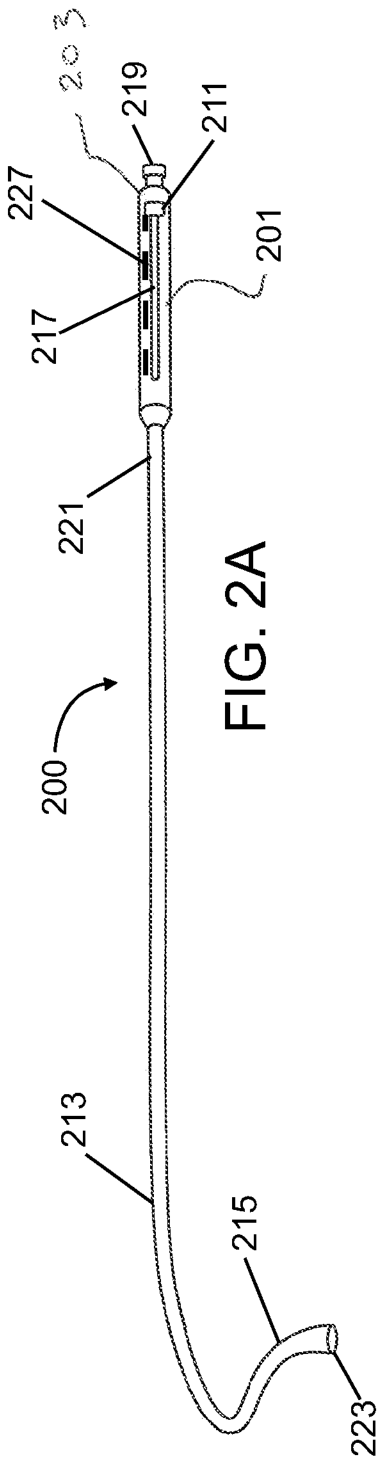
FIG. 2A shows an embodiment of a catheter device according to the present technology in a retracted state.
Figure 2B:
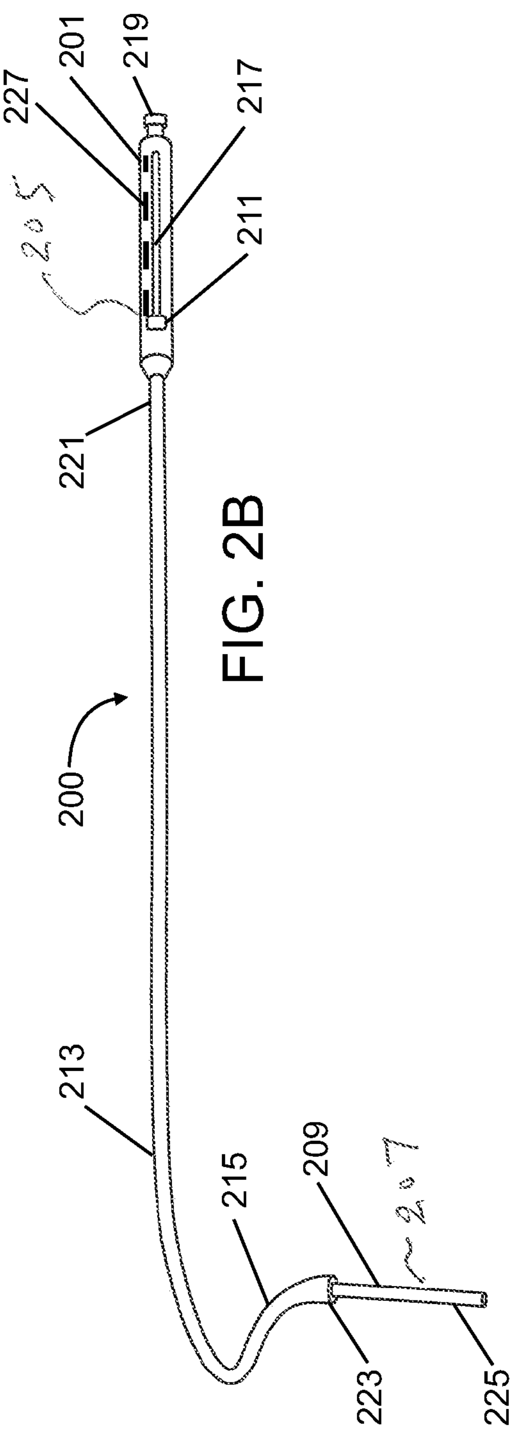
FIG. 2B shows an embodiment of a catheter device according to the present technology with a control mechanism including a slide handle in extended position.

FIGS. 2A and 2B show another embodiment of a catheter device 200. In FIG. 2A, a slider style control mechanism 201 is shown when an inner tubular member 209 is in a fully retracted position with a slider 211 in its most proximal position 203. An outer tubular member 213 is shown with a shaped distal end 215. In FIG. 2B, the slider style control mechanism 201 is shown in its most distal position 205 corresponding to the inner tubular member 209 in its most extended position 207.

As shown in FIGS. 2A and 2B, the available range of movement of the inner tubular member 209 is limited by the design of the control mechanism 201, an open slot 217 in the control mechanism 201 precisely defines the longitudinal range of movement of the inner tubular member 209. This slot 217 feature defines the range of travel and frees the operator from having to take his/her eyes away from other tasks to manipulate the inner tubular member 209 position. In addition, in other embodiments a rail, slot, or other means can be incorporated to ensure only longitudinal range of movement occurs in a similar manner to that shown in FIGS. 2A and 2B. Use of a rail or slot 217 can preclude rotational movement of the control mechanism 201 and inner tubular member 209, which may confuse an operator manipulating the catheter device 200, thus possibly creating an unwanted distraction requiring the attention of the operator.

Markings shown at 227 can provide a unit of measure or scale for the user to see the amount of extension of the inner tubular member 209 extending from the outer tubular member 213. Such markings 227 can be integrated into the housing and/or applied onto the control mechanism 201. The markings 227 can include various indicia, including numbers, graduations, symbols, coloration, etc. In certain embodiments, the markings 227 directly correspond to a length that the inner tubular member 209 extends from the shaped distal end 215 of the outer tubular member 213 in positioning the slider 211 relative to the markings 227.

With further respect to the outer tubular member 213, as shown in FIGS. 2A and 2B, the outer tubular member 213 is configured as a catheter shaft having the shaped distal end 215 designed to facilitate access to a target vessel, such as a coronary artery ostium. Examples of the shaped distal end 215 can include a Judkins right or Amplatzer left guide configurations, among others. The outer tubular member 213 is sealed to prevent air ingress/egress. The outer tubular member 213 is also immovably affixed to the control mechanism 201 and/or a hub 219. The outer tubular member 213 can be a composite shaft tubing (not shown) comprised of a PTFE (trade name TEFLON) liner to serve as the innermost layer of the outer tubular member 213, a braid, and an overcoat to seal the braid into a cohesive structure. A stainless steel braid may be woven onto the aforementioned PTFE liner. The braid material may be made from any grade of stainless steel, such as 302, 304, or 316LV. Other metals such as nitinol are also contemplated for use. In addition, other materials can be used for the braid including polymeric materials like polyamide (trade name NYLON) or liquid crystal monofilament polymer (LCP). Non-ferrous and non-metallic braid material may be used to make the device MM compatible. The "PIC" count of the braid may be varied to optimize the flexibility and torque characteristics of the outer tubular member 213. The PIC count can vary at the shaped distal end 215, where more flexibility may be desired, and at a proximal end 221 where greater stiffness may be desired. "PIC" refers to the amount of times the braiding crosses itself, in crosses per inch, for a woven pattern. A higher PIC count improves catheter shaft flexibility and a lower PIC count increases catheter shaft stiffness. The PIC count can be varied within a specified length to provide variable flexibility.

An overcoat can be applied to the braid and PTFE liner. The overcoat can be extruded onto the braided liner or it can be applied using separate segments of tubular material and fused together using a heat process with a shrink tubing cover. Other known methods of outer tubular member construction are anticipated. The overcoat can be comprised of any number of suitable biocompatible polymers familiar to those in the art. Polymers include polyether block amide or PEBA, also known by its trade name PEBAX, available from ARKEMA, which is available in several grades ranging in stiffness from a Shore D hardness of 27 and a flexural modulus of 12 MPA to a Shore D hardness of 69 or higher with a flexural modulus of 513 MPA or higher. Available grades of PEBAX range from soft to stiff, PEBAX 2533 to 7433. Other suitable materials such as thermoplastic urethanes, such as Pellathane, from Lubrizol can also be used. One example configuration includes a proximal shaft made from Pebax 7233, to provide axial stiffness, attached to a softer distal segment made of PEBAX 3533, to reduce stiffness. Any combination of polymer segments can be used to optimize the catheter shaft flexibility and stiffness both at the distal segment, the proximal segment, and anywhere in between.

An extreme distal tip 223 of the outer tubular member 213 can be made atraumatic by forming it from a soft grade of polymer such as PEBAX 2533 or 3533. The tip 223 can be fused together as described above. The extreme distal tip 223 of the outer tubular member 213 can be loaded with radiopaque material, such as barium sulfate, loaded into PEBAX at a mass or volume percentage of 20 percent or more to make the tip 223 highly visible under fluoroscopy. Other loading percentages, either by weight or volume, can make the 223 tip more or less visible under fluoroscopy.

The shaped distal end 215 of the outer tubular member 213 can be preformed into any number of desirable shapes. Shapes can include Judkins Right in 3, 4, 5 or the shape may be an AL-1 or AL-2 or AL-3. Other guide catheter tip shapes, defined by nomenclature understood by device operators, can be preformed into the shaped distal end 215. The shaped distal end 215 can be formed with a shaped forming mandrel inserted into the outer tubular member 213 and then baked at an elevated temperature for a specified period of time prior to assembly with the inner tubular member 209. Various temperature and oven bake times can be used to preform the shaped distal end 215 of the outer tubular member 213. This can be done prior to assembly with the inner tubular member 209 and is well understood by those familiar with the art.

In an alternative embodiment, the outer tubular member 213 can be deflectable. Thus, additional controls in the control mechanism 201 can be incorporated to actuate a pull wire/distal anchor ring assembly incorporated into the outer tubular member 213. The pull wire of the pull wire assembly may be sheathed in a PTFE liner to promote smooth actuation. The pull wire assembly and teflon sheath may be inserted through a dedicated lumen in the outer tubular member 213 wall. A single and double pull wire configuration is anticipated enabling both unidirectional and bidirectional steering. Any number of lumens could be incorporated into the outer tubular member 213 wall. For example, four lumens incorporated into the wall can enable four axis steering. It is also contemplated that the inner tubular member 209 can be likewise configured to enable deflection. Similarly, one or more lumens integrated into the wall of the inner tubular member 209 can house a pull wire mechanism to facilitate inner tubular member 209 deflection.

Either the inner tubular member 209 or the outer tubular member 213 can be deflectable. It is also contemplated that both the inner tubular member 209 and the outer tubular member 213 can be deflectable. This arrangement of deflectable inner and outer tubular members 209, 213 integrated with the control mechanism 201, for example the slotted configuration, ensures that deflection of the inner and outer members 209, 213, relative to the other, remains unchanged. For example, the outer tubular member 213 can be designed to deflect in a posterior and anterior direction, while the inner tubular member 209 can be configured to deflect exactly 90 degrees from the outer tubular member 213, resulting in movement in a superior and inferior direction. Thus, precise and repeatable placement of the catheter device extreme distal tip 223 within the anatomy is possible.

With further respect to the inner tubular member 209, the following aspects can be considered. The inner tubular member 209 can include an assembly designed to move the inner tubular member 209 relative to the outer tubular member 213. In this way, a distal end 225 of the inner tubular member 209 can extend past the shaped distal end 215 of the outer tubular member 213. When used in the body, the distal tip 223 of the outer tubular member is positioned near or at the ostium of a coronary artery, then the distal end 225 of the inner tubular member 209 is advanced into the coronary artery to enhance catheter support. It is also contemplated that the catheter device 200 can be used in other areas of the body. The inner tubular member 209 is designed to extend from 10 to 40 cm past the distal end of the outer tubular member, depending on the control mechanism 201 position. However, the extendable range can be made any other length to better accommodate specific applications. The slider 211 can be immovably coupled to the inner tubular member 209 to enable an operator to precisely control a length the inner tubular member 209 extends from the outer tubular member 213.

Figure 3A:
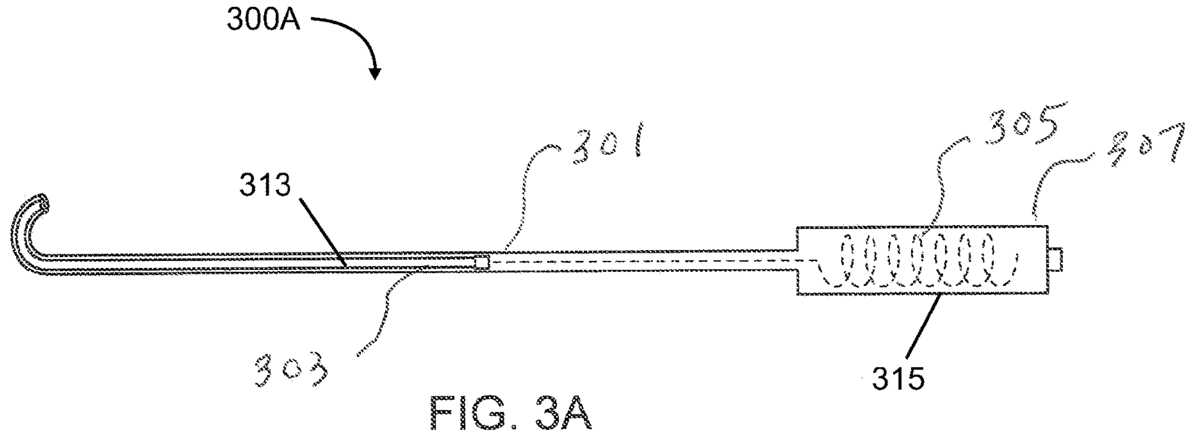
FIG. 3A shows an embodiment of a catheter device according to the present technology depicting inner components thereof, including a push wire in coiled form.
Figure 3B:
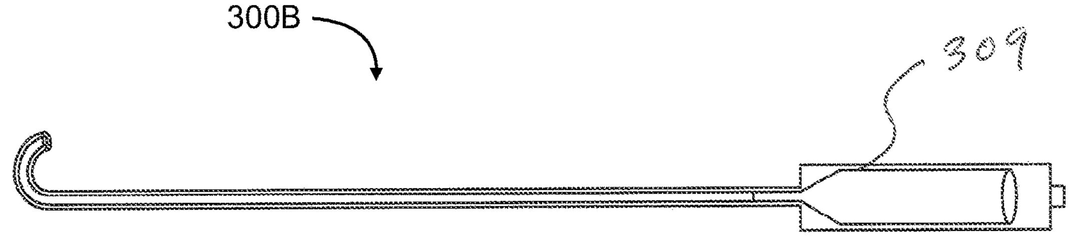
FIG. 3B shows an embodiment of a catheter device according to the present technology depicting inner components thereof, including an actuator.
Figure 3C:
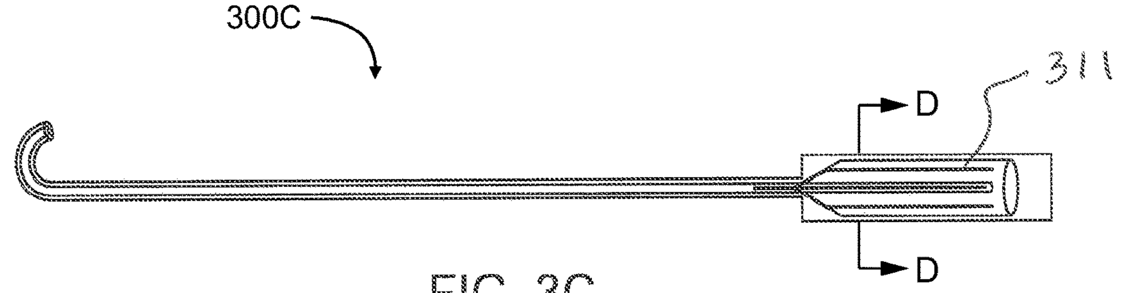
FIG. 3C shows an embodiment of a catheter device according to the present technology depicting inner components thereof, including a plurality of actuators.
Figure 3D:
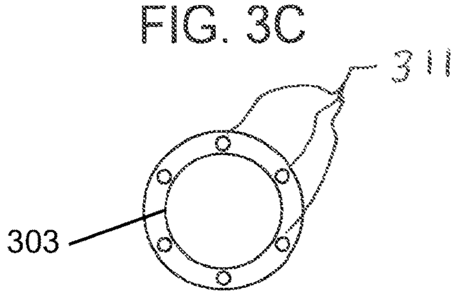
FIG. 3D shows a cross-section of an embodiment of the catheter device according to FIG. 3C depicting inner components thereof, including six actuators, wherein the view of FIG. 3D is taken from the perspective of section lines D-D in FIG. 3C.

Other embodiments of catheter devices 300A, 300B, and 300C are shown in FIGS. 3A, 3B, and 3C, which depict views through an outer tubular member 301 drawn to reveal different embodiments of an inner tubular member 303 and other internal components. The inner tubular member 303 can include a tubular portion 313, a wire 305, which can also be a cable, coupled to both the tubular portion 313 and a control mechanism 307. The control mechanism 307 in FIG. 3A shows a larger control mechanism housing 315. FIG. 3A shows the wire 305 as a coiled wire providing a compact means to actuate the inner tubular member 303 for extension and retraction relative to the outer tubular member 301. FIG. 3B shows an alternative embodiment with a wire 309, which can also be a cable. FIG. 3C shows six wires 311, which can also be cables, arranged radially around the inner tubular member. FIG. 3D represents a cross-sectional view showing the radial arrangement of wires 311, which can also be cables, around the inner tubular member 303. Any number of wires 311 or cables, etc. can be utilized as part of the control mechanism 307 to actuate movement of the inner tubular member 303. The actuation means, described later, is coupled to the wire(s) 311, which can also be cable(s), etc. to facilitate inner tubular member 303 extension or retraction from within the outer tubular member 301.

FIGS. 4A, 4B, 4C, and 4D show alternate embodiments of catheter devices 400A, 400B, 400C, 400D, each having a low profile or small diameter control mechanism 403 compared with the embodiments of FIGS. 3A-D. A see-through view of an outer tubular member 409 shows the inner tubular member assembly 401 more clearly. The inner tubular member assembly 401 is coupled to the control mechanism 403 via a wire or cable in straight 405 or coiled form 407. Means of actuation are illustrated in other figures.

Figure 4A:
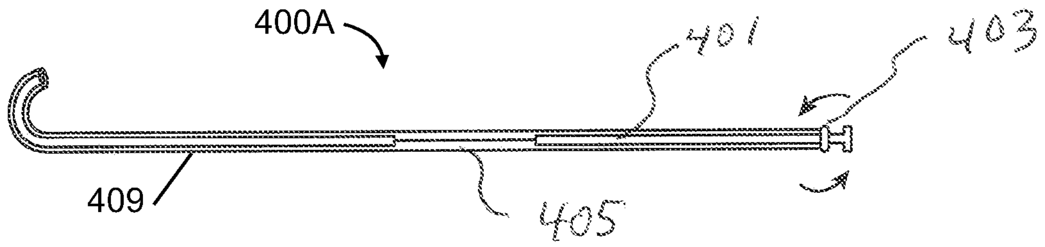
FIG. 4A shows an embodiment of a control mechanism for an inner tubular member extension according to the present technology, including a rotating control mechanism with wire actuators and an inner tubular member in a retracted state.
Figure 4B:
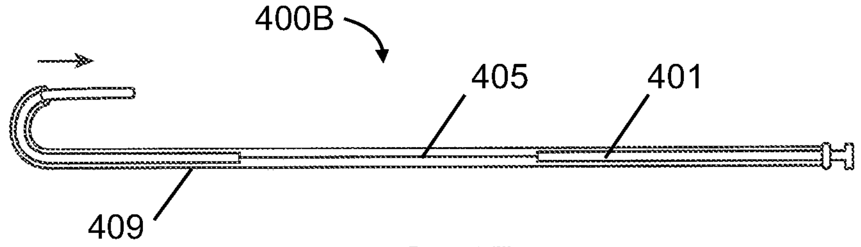
FIG. 4B shows the embodiment of the control mechanism for the inner tubular member of FIG. 4A with wire actuators in an extended state.
Figure 4C:
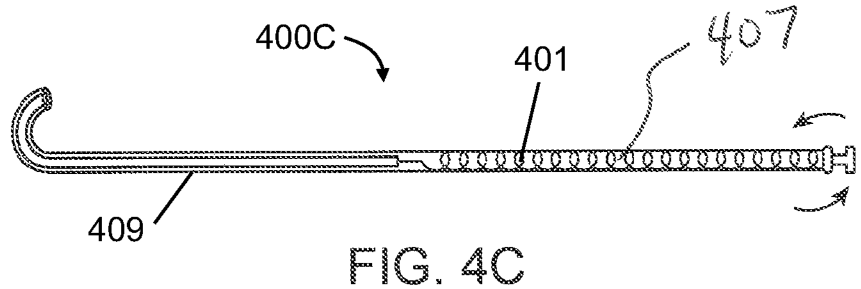
FIG. 4C shows an alternative embodiment of a control mechanism for an inner tubular member extension according to the present technology, including a rotating control mechanism with coiled actuators in retracted state.
Figure 4D:
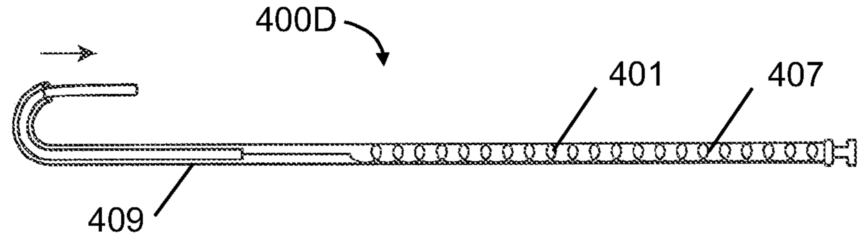
FIG. 4D shows the inner tubular member of FIG. 4C with coiled actuators in extended state.

FIG. 4A shows a rotating control mechanism 403, the movement highlighted by curved arrows, with one or more wires 405, which can also be cables, and the inner tubular member 401 in the retracted state. FIG. 4B shows the inner tubular member 401 in FIG. 4A with the wires 405 in an extended state. FIG. 4C shows an alternative embodiment with a rotating control mechanism 403 with one or more coiled wires 407 in a retracted state. FIG. 4D shows the inner tubular member in FIG. 4C with the coiled wires 407 in an extended state. The coiled wires 407 can be used to reduce the needed space inside the control mechanism 403, making it possible to shorten the housing of the control mechanism 403.

Figure 5A:
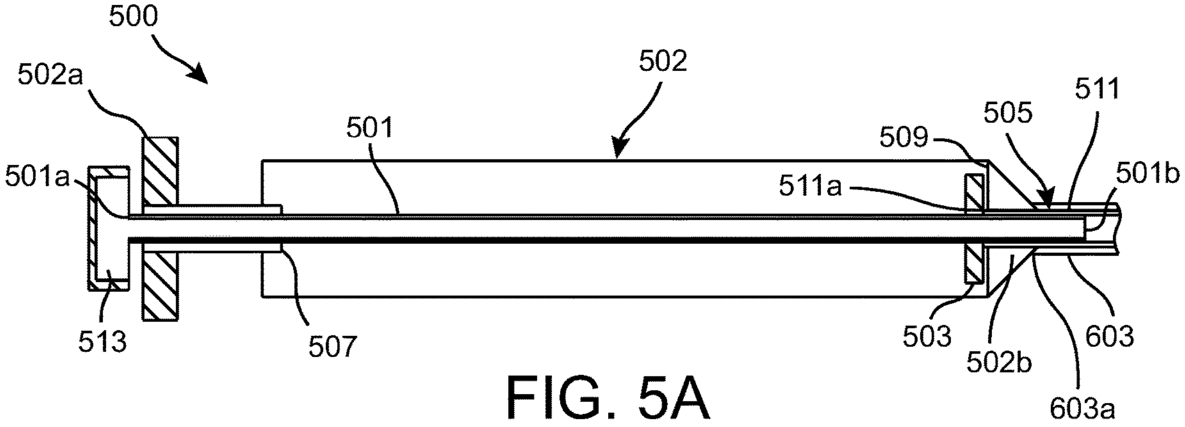
FIG. 5A shows a telescoping assembly according to the present technology having two concentric tubes, one able to slide over another (the outer tubular member is omitted for clarity), where the telescoping tubes are extended.
Figure 5B:
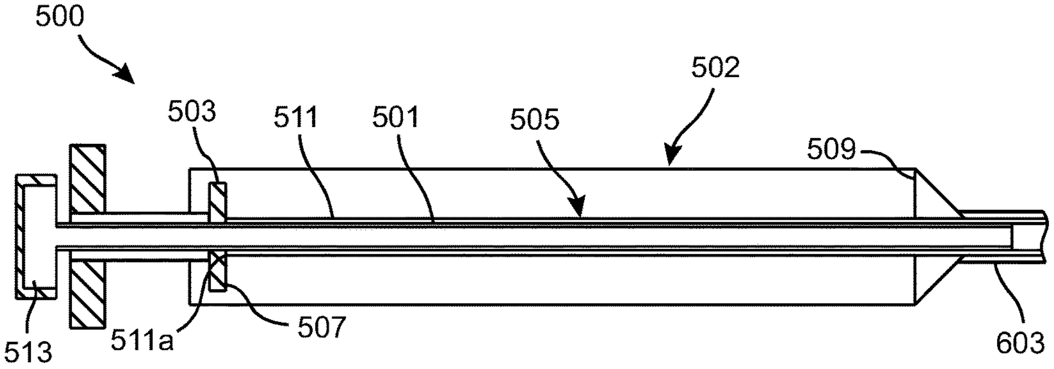
FIG. 5B shows the telescoping assembly of FIG. 5A, where the telescoping tubes are retracted.

FIGS. 5A and 5B show an embodiment of a catheter device 500 according to another embodiment of the present invention. The catheter device 500 includes a housing 502 that extends longitudinally between a proximal end 502*a* and a distal end 502*b* thereof. The housing 502 defines a proximal stop 507 disposed towards the proximal end 502*a* thereof as well as a distal stop 509 disposed towards the distal end 502*b* thereof, wherein the proximal stop 507 and the distal stop 509 are spaced apart from each other with respect to the longitudinal direction of the housing 502, which also corresponds to an axial direction of each of a fixed tubular segment 501 and a portion of an inner tubular member 511 disposed between the proximal and distal ends 502*a*, 502*b* of the housing 502. The proximal end 502*a* of the housing 502 includes a luer or hub 513 provided as an interface fitting designed to attach an accessory to the catheter in a sealed manner, wherein the luer or hub 513 may provide mechanical or fluid access to an inner luminal space formed within the catheter device 500, as described in greater detail hereinafter.

The fixed tubular segment 501 includes a proximal end 501*a* that is immovably coupled to the housing 502 and/or to the luer or hub 513 at a position at or adjacent the proximal end 502*a* of the housing 502 and a distal end 501*b* that is spaced apart and disposed towards the distal end 502*b* of the housing 502. In the illustrated embodiment, the luer or hub 513 is immovably coupled to the housing 502 at the proximal end 502*a* thereof and the proximal end 501*a* of the fixed tubular segment 501 is immovably coupled to the luer or hub 513, but alternative configurations may be utilized so long as the fixed tubular segment 501, the housing 502, and any fixed portion of a corresponding luer or hub 513 maintain fixed positions relative to one another at the proximal end 502*a* of the housing 502. The proximal end 501*a* of the fixed tubular member 501 is sealed to the corresponding surface of the housing 502 and/or the luer or hub 513 to seal the inner luminal space thereof. The distal end 501*b* of the fixed tubular member 501 is disposed axially beyond the distal end 502*b* of the housing 502 at a position exterior to the housing 502. The distal end 501*b* of the fixed tubular segment 501 is disposed axially beyond the distal stop 509 formed by the housing 502 to ensure that the inner tubular segment 501 is present along the range of motion of the inner tubular member 511 corresponding to the axial distance present between the opposing stops 507, 509. Similarly, the proximal stop 507 may be disposed towards (closer to) the distal end 502*b* of the housing 502 relative to the proximal end 501*a* of the fixed tubular segment 501 to ensure that the inner tubular segment 501 is present along the range of motion of the inner tubular member 511 corresponding to the axial distance present between the opposing stops 507, 509.

An outer tubular member 603 of the catheter device 500 extends axially away from the housing 502 at the distal end 502*b* thereof. The outer tubular member 603 includes a proximal end 603*a* that is immovably coupled to the housing 502 at or adjacent the distal end 502*b* thereof and a distal end 603*b* that is spaced apart from the distal end 502*b* of the housing 500. The proximal end 603*a* may be immovably coupled to the housing 502 at a position disposed axially distally beyond the distal stop 509 as defined by the housing 502.

The catheter device 500 includes a telescoping feature 505 wherein the proximal stop 507 and the distal stop 509 define a range of movement for the inner tubular member 511 as the inner tubular member 511 is slid relative to each of the fixed tubular segment 501 and the outer tubular member 603. The telescoping feature 505 is comprised of a plurality of concentric tubular segments designed to slide over each other in order to beneficially reduce the length of the catheter device 500. The telescoping feature 505 includes at least a portion of a length of the inner tubular member 511 being telescopically (slidably) disposed over (around) the fixed tubular segment 501 and a portion of the length of the inner tubular member 511 being telescopically (slidably) disposed within the outer tubular member 603. As such, the inner tubular member 511 includes an inner diameter that is greater than an outer diameter of the fixed tubular segment 501 to form a relatively small radial clearance for facilitating the telescopic/sliding relationship present therebetween, and the outer tubular member 603 includes an inner diameter that is greater than an outer diameter of the inner tubular member 511 to also form a relatively small radial clearance for facilitating the telescopic/sliding relationship present therebetween.

The catheter device 500 includes a reduced profile due to the compact construction of the fixed tubular segment 501, the inner tubular member 511, and the outer tubular member 603. That is, the inner tubular member 511 is received directly over (radially outwardly of) the fixed tubular segment 501 absent an intervening radially disposed element and the inner tubular member 511 is received directly within (radially inwardly of) the outer tubular member 603 absent an intervening radially disposed element, thereby reducing a radial thickness of the overlapping portions of the components 501, 511, 603. The reduced thickness of these overlapping components 501, 511, 603 can accordingly allow for an increased inner diameter of the inner luminal space formed by the components 501, 511, 603 in conjunction with a reduced outer diameter of the outer tubular member 603. The described assembly can accordingly accommodate tasks requiring an especially narrow catheter device, such as when dealing with particular narrow blood-vessels, while still providing a relatively large inner luminal space for delivering any of a number of desired therapeutic devices to the desired location within the patient.

The inner tubular member 511 is immovably coupled to a stop element 503, which extends radially outwardly relative to an outer surface of the inner tubular member 511. The stop element 503 may be immovably coupled to a proximal end 511*a* of the inner tubular member 511 disposed towards the proximal end 502*a* of the housing 502. The stop element 503 can be affixed to the inner tubular member 511 by swaging, crimping, heat bonding, adhesive bonding, and/or any other means of fastening components together. The stop element 503 is configured to define the range of axial motion of the inner tubular member 511 relative to the fixed tubular segment 501 over which the inner tubular member 511 is received. The stop element 503 extends radially outwardly such that the stop element 503 selectively contacts the distal stop 509 when the inner tubular member 511 is slid axially to a distal most position (shown in FIG. 5A) correlating to the maximum extension of the inner tubular member 511 beyond the outer tubular member 603 or the proximal stop 507 when the inner tubular member 511 is slid axially to a proximal most position (shown in FIG. 5B) corresponding to the inner tubular member 511 being fully retracted relative to the outer tubular member 603.

The telescoping feature 505 of the inner tubular member 511 includes at least one fixed tubular segment 501 sealed to a luer or hub 513 and at least one slidable tubular segment in the form of the inner tubular member 511. However, it is anticipated that additional slidable telescoping segments can be incorporated in the inner tubular member 511 assembly, as desired.

The housing 502 and the stop element 503 may include the configuration of the control mechanism 201 shown and described with reference to FIGS. 2A and 2B wherein the stop element 503 forms the slider 211 and the stops 507, 509 are defined as the opposing ends of a slot 217, a rail, or the like along which the slider/stop element 503 is configured to slide. At least a portion of the slider/stop element 503 may extend radially outwardly out of the housing 502, such as through the corresponding slot or opening 217 formed therein, for access to the slider/stop element 503 by an operator at a position exterior to the assembly of the fixed tubular segment 501 and the inner tubular member 511.

An inner luminal space formed through the catheter device 500 may include an interior of the fixed tubular segment 501 between the proximal and distal ends 501*a*, 501*b* thereof as well as an interior of the inner tubular member 511 between the distal end 501*b* of the fixed tubular segment 501 and a distal end 511*b* of the inner tubular member 511. In some embodiments, the inner luminal space may also be defined by a distal end portion of the outer tubular member 603 if or when the distal end 511*b* of the inner tubular member 511 is retracted proximally beyond the distal end 603*b* of the outer tubular member 603. In the other embodiments, the distal end 511*b* of the inner tubular member 511 may be at the same axial position as the distal end 603*b* of the outer tubular member 603 when the inner tubular member 511 is in the fully retracted position. In yet other embodiments, the distal end 511*b* of the inner tubular member 511 may be exposed at a position axially beyond and spaced apart from the distal end 603*b* of the outer tubular member 603 when the inner tubular member 511 is in the fully retracted position. The inner luminal space within the fixed tubular segment 501 may also be accessed via a flow space formed within the luer or hub 513 at the proximal end 502*a* of the housing 502, which is provided in a sealed fashion.

Figure 6A:
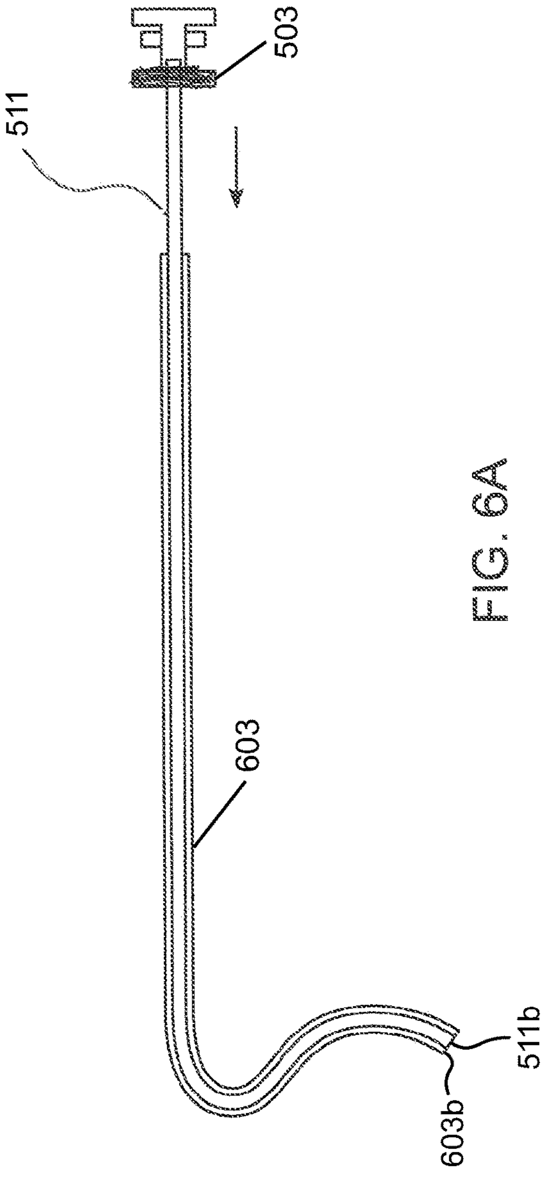
FIG. 6A is a cut-away view of an inner tubular member according to the present technology, where the inner tubular member is in a retracted state.
Figure 6B:
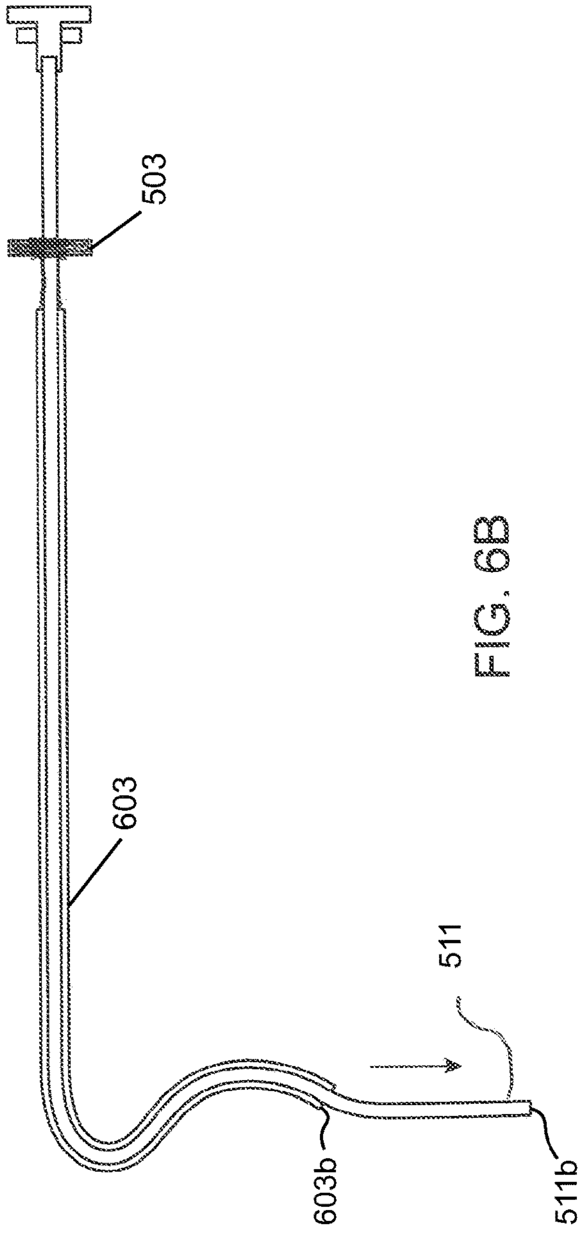
FIG. 6B shows the inner tubular member of FIG. 6A in an extended state.

The telescoping feature 505 of the inner tubular member 511 in the embodiment of FIG. 5 is shown inside the outer tubular member 603 in FIG. 6. The control mechanism housing 502 is omitted for clarity. The stop element 503 shows the position of the inner tubular member 511 relative to the outer tubular member 603 in their respective positions. In FIG. 6A, the slidable inner tubular segment of the inner tubular member 511 is shown in a retracted state and in FIG. 6B the slidable inner tubular segment of the inner tubular member 511 is shown in an extended state.

The adjustment of the inner tubular member 511 from the retracted position (with the stop element 503 abutting the proximal stop 507) to the extended position (with the stop element 503 abutting the distal stop 509) includes an inner luminal space formed by the cooperation of the interior of the fixed tubular segment 501 and then the interior of the inner tubular member 511 (at positions disposed axially beyond the distal end 501*b* of the fixed tubular segment 501) increasing in length between the proximal end 501*a* of the fixed tubular segment 501 and the distal end 511*b* of the inner tubular member 511. The described adjustment also includes a distance between the distal end 511*b* of the inner tubular member 511 and the distal end 603*b* of the outer tubular member 603 increasing in length as an increasing length of the inner tubular member 511 is exposed at positions axially beyond the distal end 603*b* of the outer tubular member 603. The described adjustment also includes a decreasing length of the inner tubular member 511 axially overlapped with the fixed tubular segment 501 as well as a decreasing length of the inner tubular member 511 axially overlapped with the outer tubular member 603 (due to the increasing extension of the inner tubular member 511 outside of the outer tubular member 603).

Figure 7A:
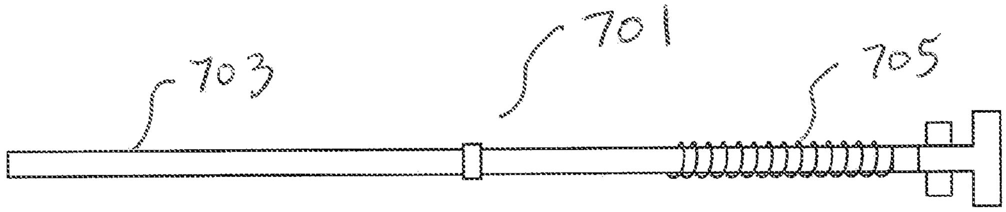
FIG. 7A shows components of an inner tubular member assembly according to the present technology, where a partially compressible inner tubular member is in an extended state.
Figure 7B:
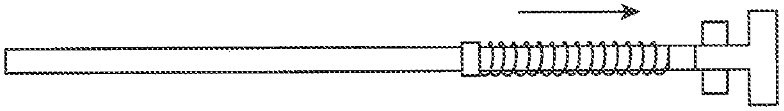
FIG. 7B shows the partially compressible inner tubular member of FIG. 7A in a retracted state.
Figure 7C:
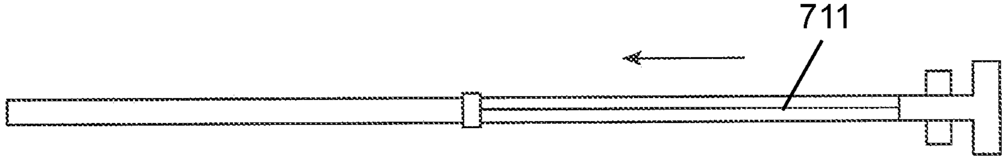
FIG. 7C shows an alternative embodiment of an inner tubular member assembly according to the present technology, including a telescoping mechanism showing concentric tubes, one sliding into another.
Figure 7D:
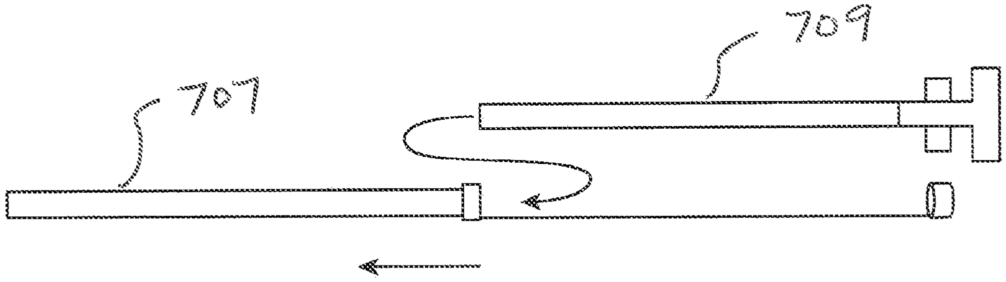
FIG. 7D shows an alternative embodiment of an inner tubular member assembly according to the present technology, including a telescoping mechanism shown with concentric tubes separated and with a single push wire.
Figure 7E:
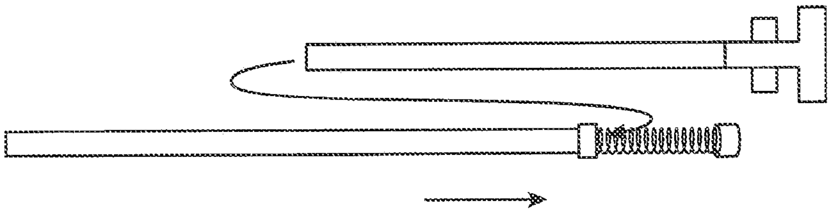
FIG. 7E shows an alternative embodiment of an inner tubular member assembly according to the present technology, including a telescoping mechanism sliding shown with concentric tubes separated and with a coiled actuation mechanism.

As shown in FIGS. 7A, 7B, 7C, 7D, and 7E, embodiments of an inner tubular member 701 can include a polymer tube 703 and a coil over tube subassembly 705. As shown in FIG. 7A, the inner tubular member 701 is in an extended state. FIG. 7B shows the compressible coil over tube subassembly 705 in a compressed state when the inner tubular member is in a retracted state. FIG. 7C shows an alternative embodiment replacing the coil over tube assembly 705 in FIG. 7A with a wire 711. In addition, as shown in FIGS. 7D and 7E, a telescoping structure, made from at least two separate inner tubular segments (e.g., as shown for FIGS. 6A-B), including at least one slidable inner tubular segment 707 and at least one non-slidable inner tubular segment 709, that can be advanced or retracted one over the other. The mechanism of actuation can compress the length of the inner tubular member 701 when retracted into the control mechanism. It is anticipated that a plurality of slidable tubes using a telescoping arrangement may be utilized to reduce the control housing length when the inner tubular member 701 is fully retracted.

Figures 8A, 8B, 8C:
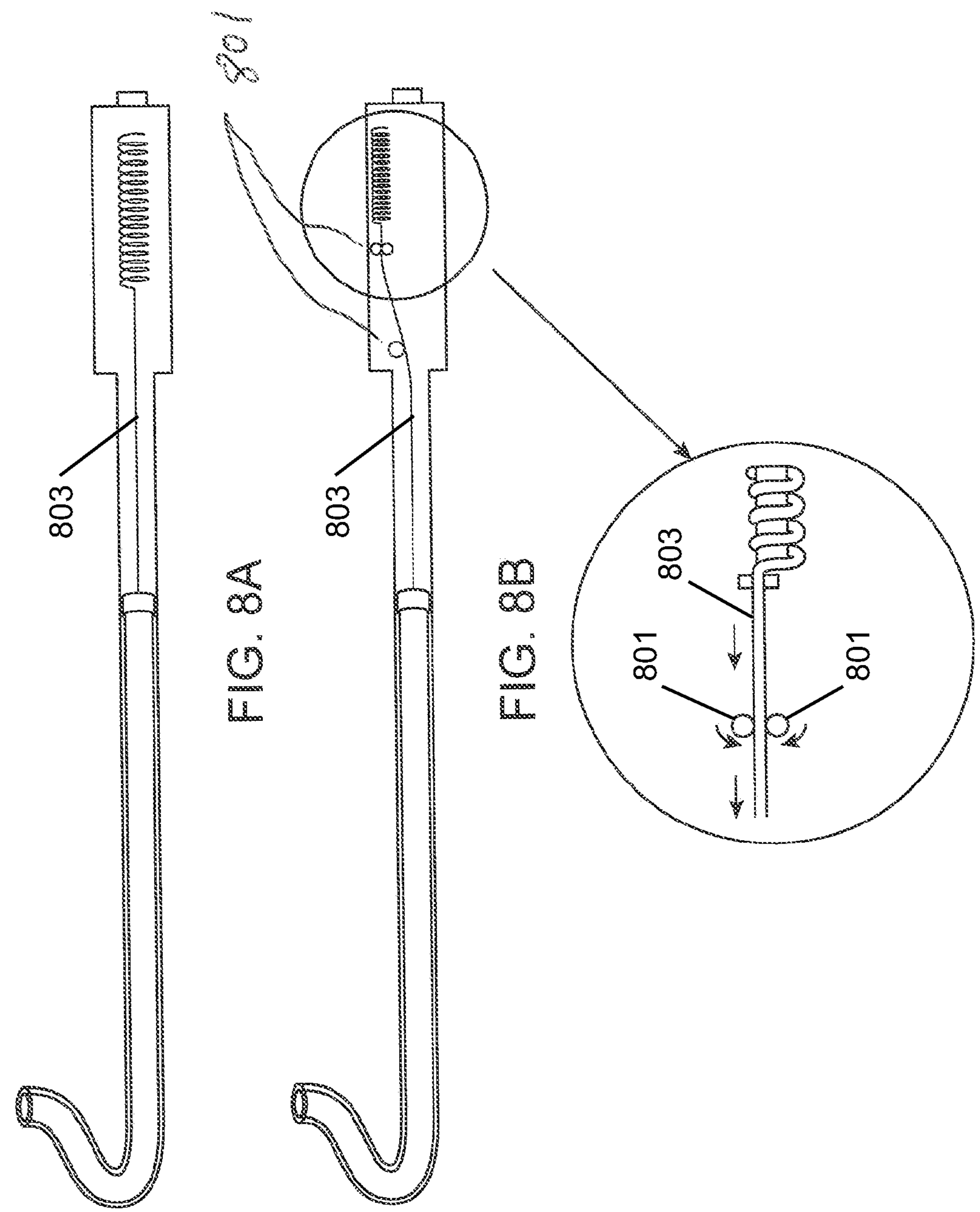
FIG. 8A shows an alternative embodiment of an actuation mechanism according to the present technology in a coiled configuration.
FIG. 8B shows an alternative embodiment of an actuation mechanism according to the present technology with a multiple pulley arrangement.
FIG. 8C shows a detailed view of the multiple pulley arrangement of FIG. 8B.

FIGS. 8A, 8B, and 8C show an embodiment using a plurality of pulleys 801 operating with at least one wire 803 to facilitate the extension or retraction of the inner tubular member and can be incorporated into the control mechanism (not shown) to facilitate extension or retraction of the inner tubular member relative to the outer tubular member.

Figure 9A:
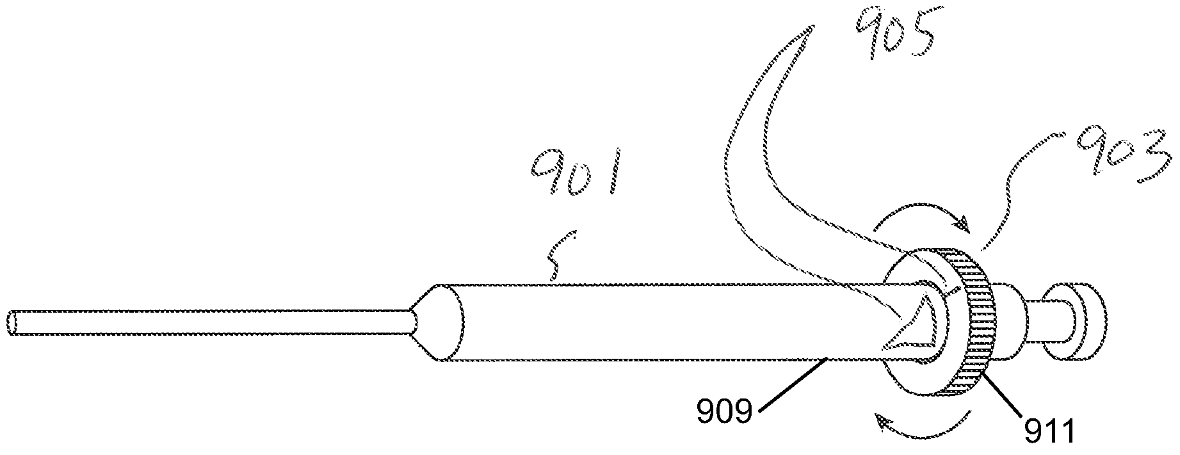
FIG. 9A shows an embodiment of a control mechanism according to the present technology having a rotating actuation mechanism.
Figure 9B:
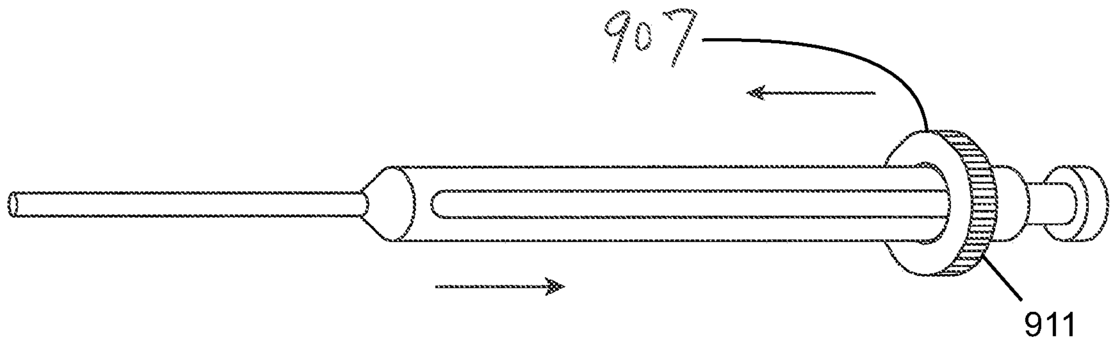
FIG. 9B shows an embodiment of a control mechanism according to the present technology having a sliding actuation mechanism.

FIG. 9A shows an embodiment of a control mechanism 901 with a rotating control ring 903. The rotating ring 903 has a series of undulations 911 on a surface thereof to improve grip. Markings 905 on the rotating ring 903 and outer control mechanism housing 909 can provide a visual indication of an extent of inner tubular member extension. Alternatively, rather than symbology, the markings can include numerical units to serve the same function. FIG. 9B shows a control mechanism 901 using an aforementioned slide mechanism 907 (e.g., FIGS. 1A-C, 2A-B) that also incorporates undulations 911 to promote improved grip.

Figure 10A:
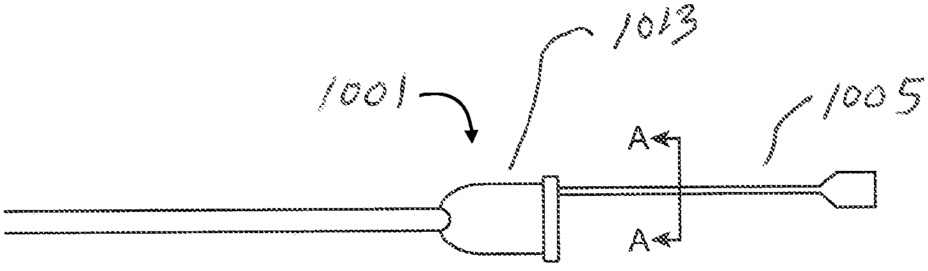
FIG. 10A shows an alternative embodiment of a pushrod mechanism according to the present technology integrated into a luer fitting.
Figure 10B:
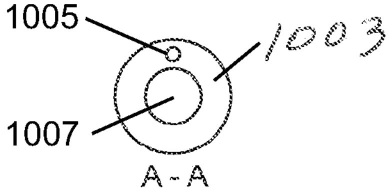
FIG. 10B shows the pushrod mechanism according to FIG. 10A with the pushrod mechanism shown outside of the inner tubular member lumen.
Figure 10C:
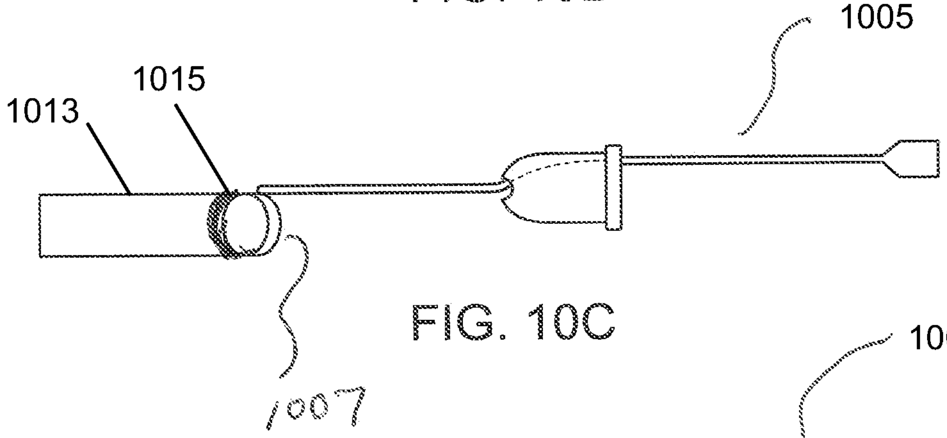
FIG. 10C shows the pushrod mechanism according to FIG. 10A with the pushrod assembly in a retracted state (outer tubular member omitted for clarity).
Figure 10D:
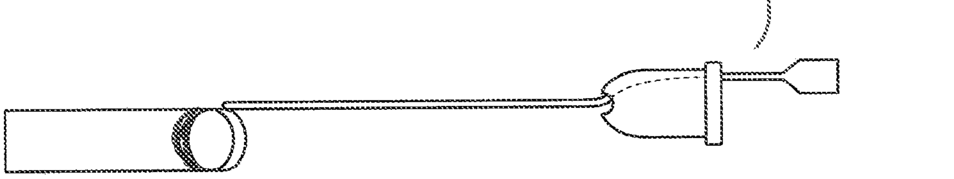
FIG. 10D shows the pushrod mechanism according to FIG. 10A with the pushrod assembly in an extended state (outer tubular member omitted for clarity).

FIGS. 10A, 10B, 10C, and 10D show an alternative embodiment of a control mechanism 1001 including a pushrod 1005 routed outside the inner tubular member lumen 1007, which is depicted in FIG. 10B showing an end view of the control mechanism 1001 shown from the perspective of the cut line A-A in FIG. 10A. In other words, the pushrod 1005 enters the luer or hub 1003 outside the lumen 1007. This enables the luminal space 1007 to be utilized by other devices. The pushrod 1005 is coupled to the inner tubular member 1013 via an anchor ring 1015 or other means to immovably fasten the pushrod 1005 to the inner tubular member 1013. The pushrod 1005 actuates the inner tubular member 1013 movement. FIG. 10C shows the position of the pushrod 1005 maximally extended toward the operator and the inner tubular member 1013 is fully retracted. When the pushrod 1005 is maximally advanced into the luer 1003 the inner tubular member 1013 is fully extended past the outer tubular member (not shown).

Another embodiment can be comprised of a plurality of inner tubular segments concentrically arranged to slide one over another, so the inner tubular member becomes shorter or longer when actuated by the pushrod 1005 or other actuating means; e.g., FIGS. 5A-B, 6A-B. The pushrod 1005 can be located outside the inner lumen 1007 to preserve the luminal space for delivering guidewires and catheters. The pushrod 1005 can be coupled to the inner tubular member by different means, such as an anchor ring 1015 immovably affixed to the inner tubular member. Other configurations coupling the pushrod 1005 to the inner tubular member are possible.

Figure 11A:
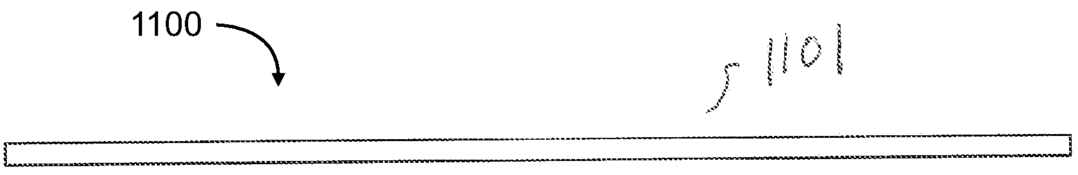
FIG. 11A shows an embodiment of an inner tubular member according to the present technology, where a partially compressible inner tubular member is in an extended state.
Figure 11B:
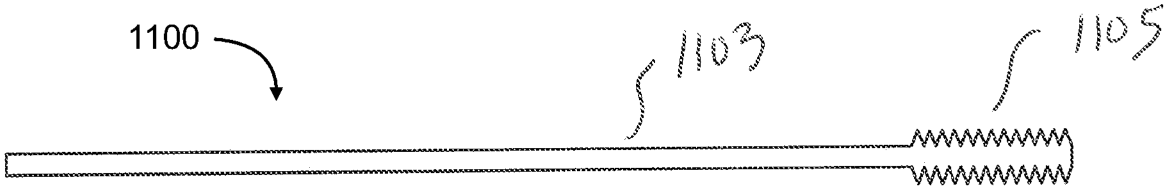
FIG. 11B shows an embodiment of an inner tubular member according to the present technology, where a partially compressible inner tubular member is in a retracted (shortened) state.

In yet another embodiment shown in FIGS. 11A and 11B, the inner tubular member 1100 can have both an extended and retracted state. This is accomplished by the use of a compressible bellows tube, where the inner tubular member 1100 may be comprised of a partially compressible member formed from a bellows structure. FIG. 11A shows the partially compressible member in a fully extended state 1101. FIG. 11B shows the partially compressible member in a compressed state 1103. A compressible bellows segment 1105 of the inner tubular member 1100 can reside in the control mechanism, joined or fused to a incompressible member that can extend past the control mechanism. In this way, a shorter control mechanism is possible. The advantage of a compressible, or collapsible, inner tubular member 1100 is to reduce the total catheter device length. A collapsible section can range from a few millimeters to over 40 centimeters. More preferably, it is intended to collapse from 5-20 centimeters.

Figure 11C:
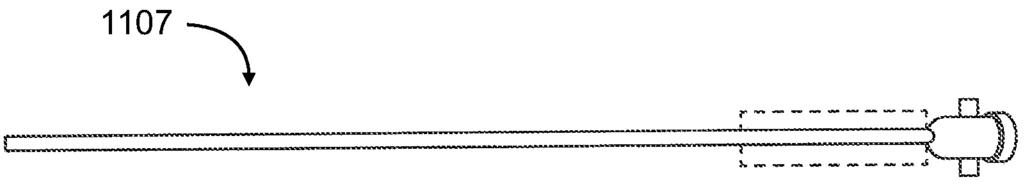
FIG. 11C shows an embodiment of an inner tubular member according to the present technology, depicting a location of a control housing (outlined) when the inner tubular member is in an extended state.
Figure 11D:
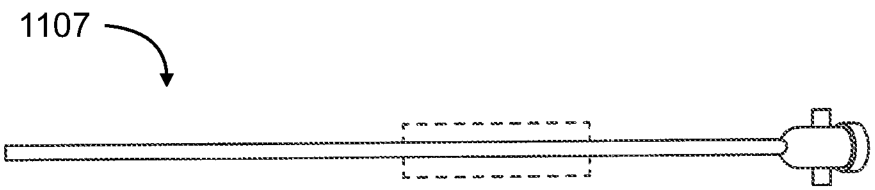
FIG. 11D shows an embodiment of an inner tubular member according to the present technology, depicting a location of a control housing (outlined) when the inner tubular member is in a retracted state.

In an alternative embodiment shown in FIGS. 11C and 11D, an incompressible inner tubular member 1107 can slide, proximal to distal, within the outer tubular member (not shown) so a portion of the inner tubular member extends from the outer tubular member. This simple arrangement offers the benefit of a lower manufacturing cost.

FIGS. 12-20 illustrate an exemplary embodiment of the catheter device 500 having the telescoping feature 505 as described with reference to FIGS. 5A and 5B. The catheter device 500 of FIGS. 12-18 includes a beneficial configuration wherein each of the inner tubular member 511 and the outer tubular member 603 thereof are provided as assemblies including a plurality of longitudinally extending segments coupled to one another to provide desirable characteristics within each of the longitudinally sequenced segments. The catheter device 500 of FIGS. 12-20 also discloses additional sealing means for sealing radial spaces formed between radially adjacent layers of the concentrically arranged tubular assemblies.

The catheter device 500 includes an integrated luer or hub 513 formed at the proximal end 502*a* thereof with the luer or hub 513 extending to a position where the proximal end 501*a* of the fixed tubular segment 501 is immovably coupled thereto. The fixed tubular segment 501 extends axially from the proximal end 501*a* thereof to the distal end 501*b* thereof, which is disposed at a position distally beyond the distal end 502*b* of the housing 502. The housing 502 includes a slot 217 formed therein and extending in the axial direction thereof for guiding the motion of the stop element (slider) 503 relative to the housing 502. The opposing ends of the slot 217 define the proximal stop 507 and the distal stop 509 of the housing 502 for defining the axial range of motion of the stop element 503 relative to the housing 502. A portion of the stop element 503 extends radially outwardly beyond an outer surface of the housing 502 to allow an operator to manipulate the stop element 503 in sliding the stop element 503 in the axial direction.

Figure 12:
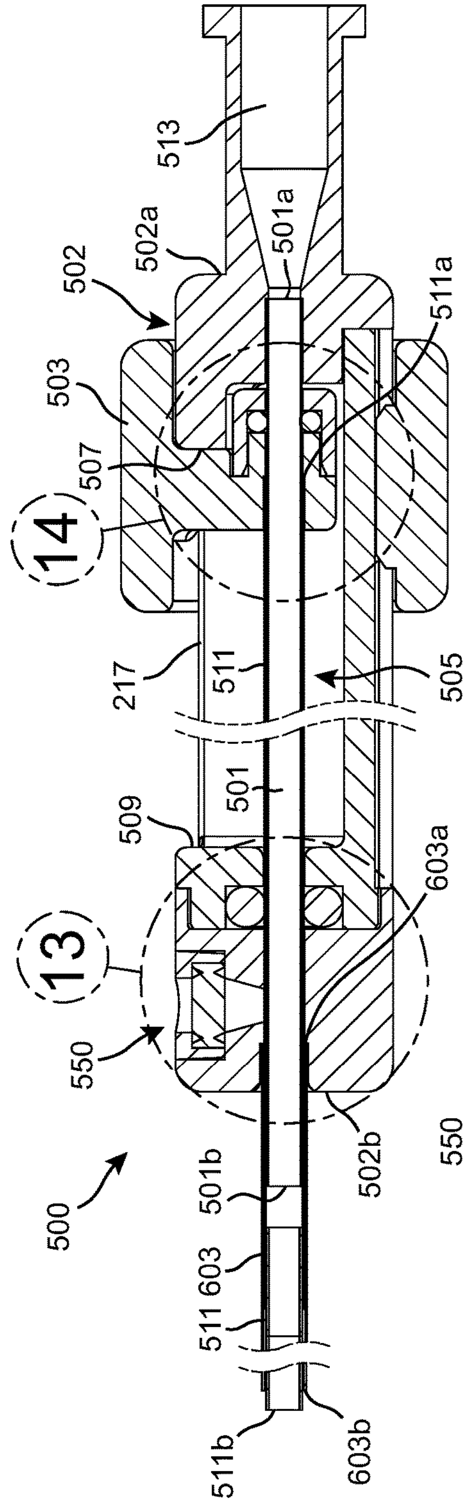
FIG. 12 shows a fragmentary elevational cross-sectional view of a catheter device according to an embodiment of the present disclosure.
Figure 14:
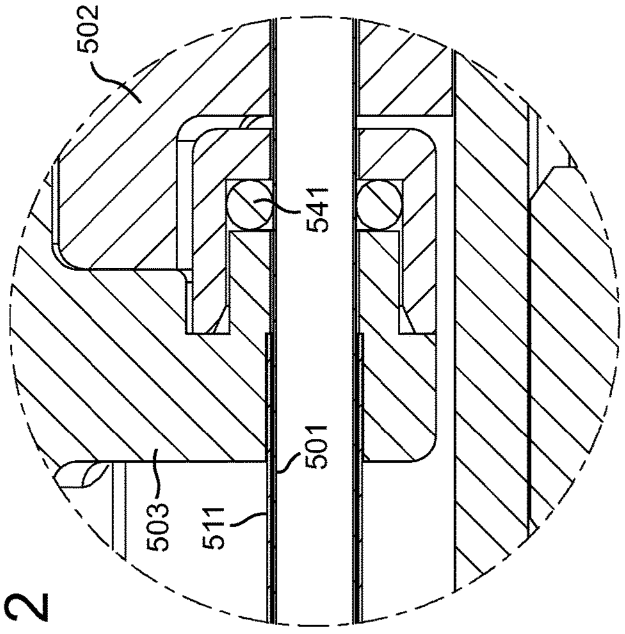
FIG. 14 shows an enlarged view of the portion of FIG. 12 as surrounded by circle 14.

The stop element 503 is shown in FIGS. 12 and 14 as including an annular groove for retaining a proximal sealing element 541. The stop element 503 is also immovably coupled to the proximal end 511*a* of the inner tubular member 511 at a distal side of the stop element 503. The proximal sealing element 541 may be provided as an O-ring disposed to extend circumferentially between an outer surface of the fixed tubular segment 501 and an inner surface of the stop element 503. The proximal sealing element 541 may be sealingly compressed between the stop element 503 and the fixed tubular segment 501 with respect to the radial direction to seal access to a space formed radially between the outer surface of the fixed tubular segment 501 and the inner surface of the inner tubular member 511. The proximal sealing element 541 is configured to slide axially along the outer surface of the fixed tubular segment 501 while maintaining the sealing effect thereof when the stop element 503 is slid therealong.

Figure 13:
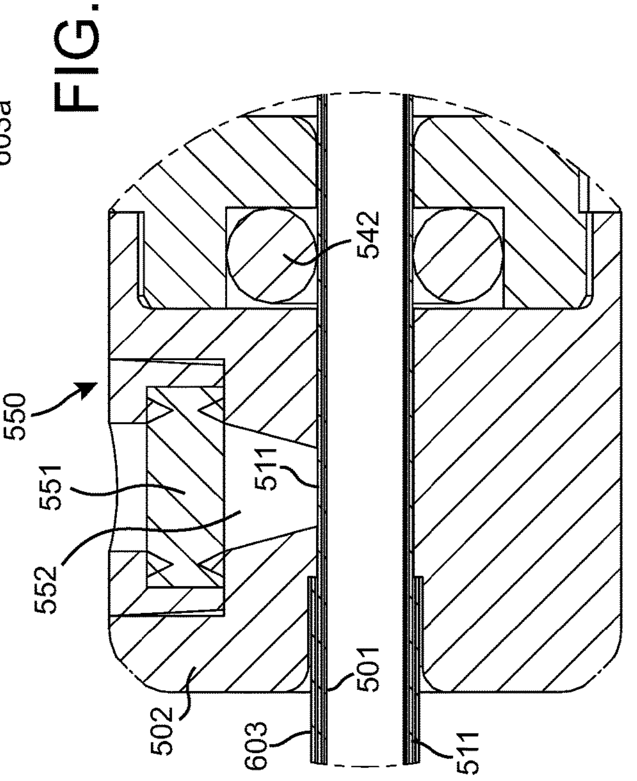
FIG. 13 shows an enlarged view of the portion of FIG. 12 as surrounded by circle 13.

The housing 502 is also shown in FIGS. 12 and 13 as including an annular groove for retaining a distal sealing element 542. The distal sealing element 542 may be provided as an O-ring disposed to extend circumferentially between an outer surface of the inner tubular member 511 and an inner surface of the housing 502. The distal sealing element 542 may be sealingly compressed between the housing 502 and the inner tubular element 511 with respect to the radial direction to seal access to a space formed radially between the outer surface of the inner tubular member 511 and the inner surface of the outer tubular member 603. The distal sealing element 542 is configured to slide relative to the outer surface of the inner tubular member 511 while maintaining the sealing effect thereof during relative motion between the inner tubular member 511 and the housing 502.

The housing 502 includes a flushing port 550 in fluid communication with the outer surface of the inner tubular member 511, wherein the outer surface of the inner tubular member 511 is in fluid communication with a radial space formed between the outer surface of the inner tubular member 511 and the inner surface of the outer tubular member 603 at a position distal from the flushing port 550. The flushing port 550 may include structure for mating the flushing port 550 with an accessory configured to supply a flushing fluid to the outer surface of the inner tubular member 511. A membrane 551 may be disposed at an inlet into an opening 552 extending to and in fluid communication with the outer surface of the inner tubular member 511. The flushing port 550 may be provided to selectively flush the radial space formed between the inner tubular member 511 and the outer tubular member 603 when the flushing fluid is delivered to the radial space via passage of the flushing fluid through the flushing port 550. The membrane 551 may be provided to resist an incidence of back-pressure causing fluid to flow back towards the exterior of the opening 552.

The proximal end 603*a* of the outer tubular member 603 is immovably coupled to the housing 502 at or adjacent the distal end 502*b* thereof. The inner tubular member 511 is configured to slide within the outer tubular member 603 and around the fixed tubular segment 501 in the manner described hereinabove to alter the total length of the inner luminal space formed by the cooperation of the fixed tubular segment 501 and the inner tubular member 511 while adjusting a position of the distal end 511*b* of the inner tubular member 511 relative to the distal end 603*b* of the outer tubular member 603. The movement of the inner tubular member 511 in the axial direction of the housing 502 is caused by the operator sliding the slider/stop element 503 along the corresponding slot 217 with the total range of motion of the slider/stop element 503 prescribed by the axial spacing present between the stops 507, 509 of the housing 502.

Figure 15:
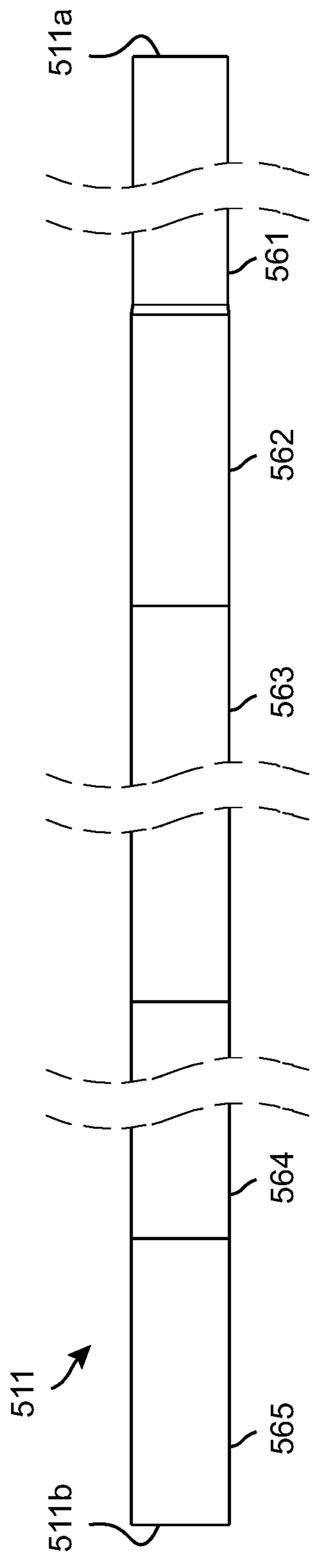
FIG. 15 is a fragmentary view showing an assembly of longitudinally extending segments forming the inner tubular member of the catheter device of FIG. 12.
Figure 16:
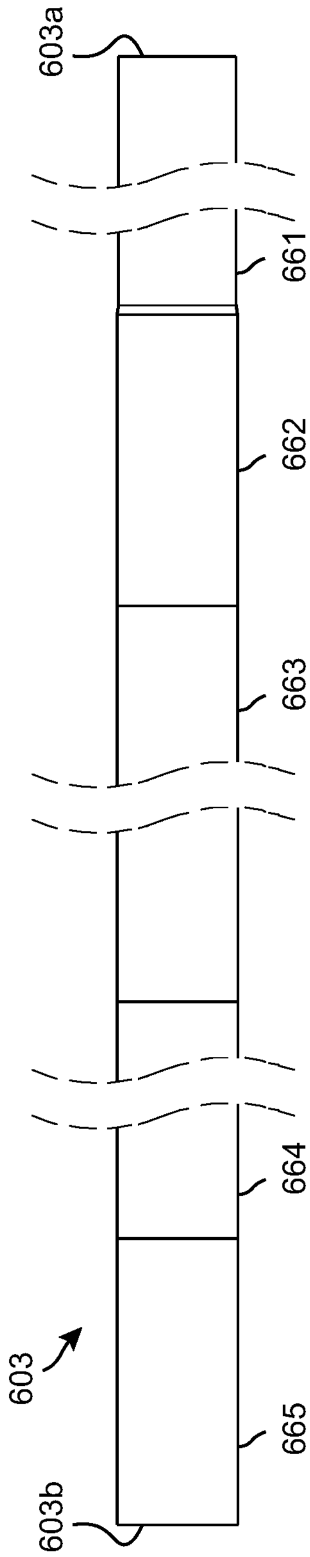
FIG. 16 is a fragmentary view showing an assembly of longitudinally extending segments forming the outer tubular member of the catheter device of FIG. 12.

As mentioned above, the inner tubular member 511 illustrated throughout FIGS. 12-20 includes a plurality of longitudinally extending segments that are coupled to one another at the ends thereof to form the resulting inner tubular member 511. As shown in FIG. 15, the inner tubular member 511 comprises, in an order from the proximal end 511*a* to the distal end 511*b* thereof, a first segment 561, a second segment 562, a third segment 563, a fourth segment 564, and a fifth segment 565. As explained hereinafter, one or more of the segments 561, 562, 563, 563, 565 may be removed from the assembly forming the inner tubular member 511 without necessarily departing from the scope of the present invention, so long as the same relationships are present between the assembly of the remaining segments 561, 562, 563, 564, 565 and the remainder of the catheter device 500 in accordance with the present disclosure. Similarly, additional segments may be added at any position along the inner tubular member 511 without necessarily departing from the scope of the present invention, so long as the use of the additional segments maintains the same relationships present between the assembly of the corresponding segments in accordance with the present disclosure. That is, the same relationships may be present between adjacent disposed segments with regards to the progression to subsequent ones of the segments while remaining within the scope of the present invention. Each of the segments described hereinafter is assumed to be tubular in structure (cylindrical) with a corresponding inner surface defining an interior thereof and an outer surface defining an exterior thereof, and each of the segments is assumed to extend a length in the axial or longitudinal direction of the inner tubular member 511 such that each of the segments occupies a portion of a total length of the inner tubular member 511.

In the present embodiment, the first segment 561, which includes the proximal end 511*a* of the inner tubular member 511, may be formed from a thermoset polymer (thermosetting plastic) to provide a smooth sliding surface for accommodating the sliding motion present between the outer surface of the fixed tubular segment 501 and the inner tubular member 511. The thermoset polymer may be a polyimide. The first segment 561 may be selected to include a length that is at least as great as the axial distance present between the opposing stops 507, 509 defined by the housing 502 to ensure smooth sliding of the inner tubular member 511 along the full range of axial motion thereof. In the present embodiment, the first segment 561 may be approximately 10 cm long. In some embodiments, the first segment 561 may include a PTFE liner as an innermost layer disposed within the polyimide, and the lining of the PTFE may include a thickness of about 0.0015 in.

The second segment 562 is disposed adjacent and distally from the first segment 561. As explained in greater detail hereinafter when describing a method of assembling the inner tubular member 511, the first segment 561 and the second segment 562 may overlap each other partially at a lap joint present therebetween to strengthen the joint via an increase in the surface area of the segments 561, 562 that are in contact with each other along the corresponding joint. The second segment 562 may be formed from a thermoplastic polymer, such as a polyamide. In the present example, the polyamide forming the second segment 562 may be Nylon 12, as a non-limiting example. The second segment 562 may include a relatively short length in comparison to the total length of the inner tubular member 511, such as being about 0.5 cm in length, or less. The second segment 562 may be provided primarily to aid in coupling the thermoset polyimide polymer formed by the first segment 561 to a thermoplastic polyamide polymer formed by the third segment 563. The second segment 562 may be provided in the absence of additional reinforcement and may be clear in appearance. In some embodiments, the second segment 562 may include a PTFE liner as an innermost layer disposed within the polyimide, and the lining of the PTFE may include a thickness of about 0.0015 in.

The third segment 563 is disposed adjacent and distally from the second segment 562. In contrast to the previously described lap joint, the second segment 562 and the third segment 563 may be joined at the respective facing ends thereof via a butt joint where the cylindrical end faces of the segments 562, 563 are axially aligned and joined to one another via a suitable heat joining process. The third segment 563 may be formed at least partially from a thermoplastic polymer, such as a polyamide. In the present example, the polyamide forming the third segment 563 may be a medical grade polyamide 12 polymer known by the trade name VESTAMID®, as a non-limiting example. The third segment 563 may be relatively long, and may form a majority of the length of the inner tubular member 511. In the present embodiment, the third segment 563 is about 74.0 cm in length.

The third segment 563 may have the same general construction as described with reference to the outer tubular member 213 hereinabove, wherein the third segment 563 may include a PTFE liner as an innermost layer, a braid, and an overcoat formed from the described polyamide polymer to seal the braid into a cohesive structure. The lining of the PTFE may include a thickness of about 0.0015 in. The wire reinforced braid may include the wire having a diameter of 0.0015 in and a PIC count of about 80. The weave pattern utilized in the braid may be an over-under (diamond) pattern. The braid material may be made from any grade of stainless steel, such as 302, 304, or 316LV. An additional stainless steel braid may be woven onto the aforementioned PTFE liner, as desired. Other metals such as nitinol are also contemplated for use with respect to either described braid. In addition, other materials can be used for the braid including polymeric materials like polyamide LCP. Non-ferrous and non-metallic braid material may be used to make the device MM compatible. The PIC count of the braid may be varied to optimize the flexibility and torque characteristics thereof. The overcoat can be applied to the braid and PTFE liner. The overcoat can be extruded onto the braided liner or it can be applied using separate segments of tubular material and fused together using a heat process with a shrink tubing cover.

The fourth segment 564 is disposed adjacent and distally from the third segment 563. The third segment 563 and the fourth segment 564 may be joined at the respective facing ends thereof via a butt joint where the cylindrical end faces of the segments 563, 564 are axially aligned and joined to one another. The fourth segment 564 may be formed at least partially from a thermoplastic polymer, such as a polyamide. In the present example, the polyamide forming the fourth segment 564 may be PEBAX 5533, as a non-limiting example. In the present embodiment, the fourth segment 564 is about 24.5 cm in length.

The fourth segment 564 may have the same general construction as described with reference to the third segment 563 hereinabove, wherein the fourth segment 564 may include a PTFE liner as an innermost layer, a braid, and an overcoat formed from the described polyamide polymer (PEBAX 5533) to seal the braid into a cohesive structure. The lining of the PTFE may include a thickness of about 0.0015 in. The wire reinforced braid may include the wire having a diameter of 0.0015 in and a PIC count of about 80 at a proximal end of the fourth segment 564 and a PIC count of about 125 at a distal end thereof. A transition from the PIC count of 80 to the PIC count of 125 may occur about 14.5 cm from the distal end of the fourth segment 564. The fourth segment 564 may further include a braid formed within the PTFE liner. The braid patterns, configurations, and materials utilized for either of the disclosed braids of the fourth segment 564 may be the same patterns, configurations, and materials described above with reference to the third segment 563.

The fifth segment 565 is disposed adjacent and distally from the fourth segment 564. The fourth segment 564 and the fifth segment 565 may be joined at the respective facing ends thereof via a butt joint where the cylindrical end faces of the segments 564, 565 are axially aligned and joined to one another. The fifth segment 565 may be formed at least partially from a thermoplastic polymer, such as a polyamide. In the present example, the polyamide forming the fifth segment 565 may be PEBAX 3533, as a non-limiting example. In the present embodiment, the fifth segment 565 is relatively short compared to the total length of the inner tubular member 511, and may be about 0.5 cm in length.

The fifth segment 565 may have the same general construction as described with reference to the third segment 563 hereinabove, wherein the fifth segment 565 may include a PTFE liner as an innermost layer, a braid, and an overcoat formed from the described polyamide polymer (PEBAX 3533) to seal the braid into a cohesive structure. The lining of the PTFE may include a thickness of about 0.0015 in. The wire reinforced braid may include the wire having a diameter of 0.0015 in and a PIC count of about 125. The fifth segment 565 may further include a braid formed within the PTFE liner. The braid patterns, configurations, and materials utilized for either of the disclosed braids of the fifth segment 565 may be the same patterns, configurations, and materials described above with reference to the third segment 563.

The distal end 511*b* of the inner tubular member 511 as formed by the distal end of the fifth segment 565 can be made atraumatic and can be loaded with radiopaque material or other fluoroscopic marker to make the distal end 511*b* highly visible under fluoroscopy. A length of about 1.5 mm of the fifth segment 565 at the distal end thereof may be devoid of one or both of the PTFE liner and the braid reinforcement to render the distal end of the fifth segment 565 as particularly flexible and soft.

The inner tubular member 511 may be assembled to include a varying degree of flexural stiffness or bending stiffness as the inner tubular member 511 extends from the proximal end 511*a* to the distal end 511*b* thereof. The varying stiffness of the inner tubular member 511 along the length thereof may be facilitated by one or more of the different disclosed segments 561, 562, 563, 564, 565 being provided to include a different bending stiffness from adjacent ones of the segments 561, 562, 563, 564, 565. Specifically, in some embodiments, at least one of a plurality of the segments forming the inner tubular member 511 includes a decreased bending stiffness relative to an adjacent one of the plurality of segments disposed towards the proximal end 511*a* of the inner tubular member 511. Stated alternatively, at least one of the plurality of segments forming the inner tubular member 511 includes an increased bending stiffness relative to an adjacent one of the plurality of segments disposed towards the distal end 511*b* of the inner tubular member 511. In some embodiments, at least three of the plurality of segments progressively include a decrease in bending stiffness towards the distal end 511*b*, or (stated otherwise) an increase in bending stiffness towards the proximal end 511*a*. In other embodiments, at least four of the plurality of segments progressively include a decrease in bending stiffness towards the distal end 511*b*, or an increase in bending stiffness towards the proximal end 511*a*. Still, in other embodiments, all five of the segments include a decrease in bending stiffness towards the distal end 511*b*, or an increase in bending stiffness towards the proximal end 511*a*. Specifically, in some embodiments, the fourth segment 564 has a greater bending stiffness than the fifth segment 565 and the third segment 563 has a greater bending stiffness than the fourth segment 564. In other embodiments, the second segment 562 also includes a greater bending stiffness than the third segment 563. In yet other embodiments, the first segment 561 additionally includes a greater bending stiffness than the second segment 562.

The present example includes each of the different segments 561, 562, 563, 564, 565 being formed, at least partially, from a different polymeric material to at least partially contribute to the different relative bending stiffness present within each of the different segments 561, 562, 563, 564, 565 as a result of the different bending stiffness associated with each of the different polymeric materials that may be utilized in forming one of the segments 561, 562, 563, 564, 565. The different polymeric materials may refer to the materials described as forming the polymeric overcoat utilized to provide the cohesive structure to each of the segments 563, 564, 565 also having a liner and a braid formed therein, or may refer to a main body material forming either of the segments 561, 562. In general, the inner tubular member 511 may include the polymeric materials forming the different segments 561, 562, 563, 564, 565 having a decreasing bending stiffness when progressing from the proximal end 511*a* towards the distal end 511*b* of the inner tubular member 511, thereby facilitating an increased flexibility of the inner tubular member 511 adjacent and towards the distal end 511*b* thereof in comparison to the proximal end 511*a* thereof.

The differing bending stiffnesses among the different segments 561, 562, 563, 564, 565 may also be facilitated by varying the PIC count of the wire braid utilized in the different segments 563, 564, 565 having such a braid, wherein an increase in the PIC count corresponds to a decrease in the corresponding bending stiffness. In the present embodiment, the PIC count varies from 80 at the proximal end of the third segment 563 to 125 at the distal end of the fifth segment 565 to promote the decrease in bending stiffness towards the distal end 511*b*.

The outer tubular member 603 illustrated throughout FIGS. 12-20 also includes a plurality of axially extending segments that are coupled to one another at the axial ends thereof to form the resulting outer tubular member 603. Specifically, the outer tubular member 603 of FIG. 16 comprises, in an order from the proximal end 603*a* to the distal end 603*b* thereof, a first segment 661, a second segment 662, a third segment 663, a fourth segment 664, and a fifth segment 665. As explained hereinafter, one or more of the segments 661, 662, 663, 663, 665 may be removed from the assembly forming the outer tubular member 603 without necessarily departing from the scope of the present invention, so long as the same relationships are present between the assembly of the remaining segments 661, 662, 663, 664, 665 and the remainder of the catheter device 500 in accordance with the present disclosure. Similarly, additional segments may be added at any position along the outer tubular member 603 without necessarily departing from the scope of the present invention, so long as the use of the additional segments maintain the same relationships present between the assembly of the corresponding segments and the remainder of the catheter device 500 in accordance with the present disclosure. That is, the same relationships may be present between adjacent disposed segments with regards to the progression to subsequent ones of the segments while remaining within the scope of the present invention. Each of the segments described hereinafter is assumed to be tubular (cylindrical) in structure with a corresponding inner surface defining an interior thereof and an outer surface defining an exterior thereof, and each of the segments is assumed to extend a length in the axial or longitudinal direction of the outer tubular member 603 such that each of the segments occupies a portion of a total length of the outer tubular member 603. The outer tubular member 603 may be formed with any of the distal end shapes including at least one curve as shown and described throughout the present disclosure, but is shown throughout FIGS. 12-16 in a substantially linear configuration for simplicity and clarity.

In the present embodiment, the first segment 661, which includes the proximal end 603*a* of the outer tubular member 603, may be formed from a thermoset polymer to provide a smooth sliding surface for accommodating the sliding motion present between the outer surface of the inner tubular member 511 and the outer tubular member 603. The thermoset polymer may be a polyimide. The first segment 661 may be selected to include a length that is at least as great as the axial distance present between the opposing stops 507, 509 defined by the housing 502 to ensure smooth sliding of the inner tubular member 511 along the full range of axial motion thereof. In the present embodiment, the first segment 661 may be approximately 10 cm long. In some embodiments, the first segment 661 may include a PTFE liner as an innermost layer disposed within the polyimide, and the lining of the PTFE may include a thickness of about 0.0015 in.

The second segment 662 is disposed adjacent and distally from the first segment 661. The first segment 661 and the second segment 662 may overlap each other partially at a lap joint present therebetween to strengthen the joint via an increase in the surface area of the segments 661, 662 that are in contact with each other along the joint. The second segment 662 may be formed from a thermoplastic polymer, such as a polyamide. In the present example, the polyamide forming the second segment 562 may be Nylon 12, as a non-limiting example. The second segment 662 may include a relatively short length in comparison to the total length of the outer tubular member 603, such as being about 0.5 cm in length. The second segment 662 may be provided primarily to aid in coupling the thermoset polyimide polymer formed by the first segment 661 to the thermoplastic polyamide polymer formed by the third segment 662. The second segment 662 may be provided in the absence of additional reinforcement and may be clear in appearance. In some embodiments, the second segment 662 may include a PTFE liner as an innermost layer disposed within the polyimide, and the lining of the PTFE may include a thickness of about 0.0015 in.

The third segment 663 is disposed adjacent and distally from the second segment 662. In contrast to the previously described lap joint, the second segment 662 and the third segment 663 may be joined at the respective facing ends thereof via a butt joint where the cylindrical end faces of the segments 662, 663 are axially aligned and joined to one another. The third segment 663 may be formed at least partially from a thermoplastic polymer, such as a polyamide. In the present example, the polyamide forming the third segment 663 may be a medical grade polyamide 12 polymer known by the trade name VESTAMID®, as a non-limiting example. The third segment 663 may be relatively long, and may form a majority of the length of the outer tubular member 603. In the present embodiment, the third segment 663 is about 89.0 cm in length.

The third segment 663 may have the same general construction as described with reference to the outer tubular member 213 hereinabove and the segments 563, 564, 565 of the inner tubular member 511, wherein the third segment 663 may include a PTFE liner as an innermost layer, a braid, and an overcoat formed from the described polyamide polymer to seal the braid into a cohesive structure. The lining of the PTFE may include a thickness of about 0.0015 in. The wire reinforced braid may include a 0.001 in×0.005 in flat wire having a PIC count of about 65. The weave pattern utilized in the braid may be an over-under (diamond) pattern. The braid material may be made from any grade of stainless steel, such as 302, 304, or 316LV. An additional stainless steel braid may be woven onto the aforementioned PTFE liner. Other metals such as nitinol are also contemplated for use with respect to either described braid. In addition, other materials can be used for the braid including polymeric materials like polyamide LCP. Non-ferrous and non-metallic braid material may be used to make the device Mill compatible. The PIC count of the braid may be varied to optimize the flexibility and torque characteristics thereof. The overcoat can be applied to the braid and PTFE liner. The overcoat can be extruded onto the braided liner or it can be applied using separate segments of tubular material and fused together using a heat process with a shrink tubing cover.

The fourth segment 664 is disposed adjacent and distally from the third segment 663. The third segment 663 and the fourth segment 664 may be joined at the respective facing ends thereof via a butt joint where the cylindrical end faces of the segments 663, 664 are axially aligned and joined to one another. The fourth segment 664 may be formed at least partially from a thermoplastic polymer, such as a polyamide. In the present example, the polyamide forming the fourth segment 664 may be PEBAX 5533, as a non-limiting example. In the present embodiment, the fourth segment 664 is about 1.0 cm in length.

The fourth segment 664 may have the same general construction as described with reference to the third segment 663 hereinabove, wherein the fourth segment 664 may include a PTFE liner as an innermost layer, a braid, and an overcoat formed from the described polyamide polymer (PEBAX 5533) to seal the braid into a cohesive structure. The lining of the PTFE may include a thickness of about 0.0015 in. The wire reinforced braid may include a 0.001 in×0.005 in flat wire having a PIC count of about 65. The fourth segment 664 may further include a braid formed within the PTFE liner. The braid patterns, configurations, and materials utilized for either of the disclosed braids of the fourth segment 664 may be the same patterns, configurations, and materials described above with reference to the third segment 663.

The fifth segment 665 is disposed adjacent and distally from the fourth segment 664. The fourth segment 664 and the fifth segment 665 may be joined at the respective facing ends thereof via a butt joint where the cylindrical end faces of the segments 664, 665 are axially aligned and joined to one another. The fifth segment 665 may be formed at least partially from a thermoplastic polymer, such as a polyamide. In the present example, the polyamide forming the fifth segment 665 may be PEBAX 3533, as a non-limiting example. In the present embodiment, the fifth segment 665 is relatively short compared to the total length of the outer tubular member 603, and may be about 0.5 cm in length.

The fifth segment 665 may have the same general construction as described with reference to the third segment 663 hereinabove, wherein the fifth segment 665 may include a PTFE liner as an innermost layer, a braid, and an overcoat formed from the described polyamide polymer (PEBAX 3533) to seal the braid into a cohesive structure. The lining of the PTFE may include a thickness of about 0.0015 in. The wire reinforced braid may include a 0.001 in×0.005 in flat wire having a PIC count of about 65. The fifth segment 665 may further include a braid formed within the PTFE liner. The braid patterns, configurations, and materials utilized for either of the disclosed braids of the fifth segment 665 may be the same patterns, configurations, and materials described above with reference to the third segment 663.

The distal end 603*b* of the outer tubular member 603 as formed by the distal end of the fifth segment 665 can be made atraumatic and can be loaded with radiopaque material to make the distal end 603*b* highly visible under fluoroscopy. A length of about 1.5 mm of the fifth segment 665 at the distal end thereof may be devoid of one or both of the PTFE liner and the braid reinforcement.

The outer tubular member 603 may be assembled to include a varying degree of flexural stiffness or bending stiffness as the outer tubular member 603 extends from the proximal end 603*a* to the distal end 603*b* thereof. The varying stiffness of the outer tubular member 603 along the length thereof may be facilitated by one or more of the different disclosed segments 661, 662, 663, 664, 665 being provided to include a different bending stiffness from adjacent ones of the segments 661, 662, 663, 664, 665. Specifically, in some embodiments, at least one of a plurality of segments forming the outer tubular member 603 includes a decreased bending stiffness relative to an adjacent one of the plurality of segments disposed towards the proximal end 603*a* of the outer tubular member 603. Stated alternatively, at least one of the plurality of segments forming the outer tubular member 603 includes an increased bending stiffness relative to an adjacent one of the plurality of segments disposed towards the distal end 603*b* of the outer tubular member 603. In some embodiments, at least three of the plurality of segments progressively include a decrease in bending stiffness towards the distal end 603*b*, or (stated otherwise) an increase in bending stiffness towards the proximal end 603*a*. In other embodiments, at least four of the plurality of segments progressively include a decrease in bending stiffness towards the distal end 603*b*, or an increase in bending stiffness towards the proximal end 603*a*. Still, in other embodiments, all five of the segments include a decrease in bending stiffness towards the distal end 603*b*, or an increase in bending stiffness towards the proximal end 603*a*. Specifically, in some embodiments, the fourth segment 664 has a greater bending stiffness than the fifth segment 665 and the third segment 663 has a greater bending stiffness than the fourth segment 664. In other embodiments, the second segment 662 also includes a greater bending stiffness than the third segment 663. In yet other embodiments, the first segment 661 additionally includes a greater bending stiffness than the second segment 662.

The present example includes each of the different segments 661, 662, 663, 664, 665 being formed, at least partially, from a different polymeric material to at least partially contribute to the different relative bending stiffness present within each of the different segments 661, 662, 663, 664, 665 as a result of the different bending stiffness associated with each of the different polymeric materials that may be utilized in forming one of the segments 661, 662, 663, 664, 665. The different polymeric materials may refer to the materials described as forming the polymeric overcoat utilized to provide the cohesive structure to each of the segments 663, 664, 665 also having a liner and a braid formed therein, or may refer to a main body material forming either of the segments 661, 662. In general, the outer tubular member 603 may include the polymeric materials forming the different segments 661, 662, 663, 664, 665 having a decreasing bending stiffness when progressing from the proximal end 603*a* towards the distal end 603*b* of the outer tubular member 603, thereby facilitating an increased flexibility of the outer tubular member 603 adjacent the distal end 603*b* thereof in comparison to the proximal end 603*a* thereof. The differing bending stiffnesses among the different segments 661, 662, 663, 664, 665 may also be facilitated by varying the PIC count of the wire braid utilized in the different segments 663, 664, 665, wherein an increase in the PIC count corresponds to a decrease in the corresponding bending stiffness.

As mentioned throughout, the outer tubular member 603 of the catheter device 500 may be provided with an outer diameter in the 5 Fr to 6 Fr range for accomplishing certain procedures contemplated herein. However, it should be apparent to one skilled in the art that the relationships disclosed herein may be utilized in conjunction with a guide catheter having different dimensions without necessarily departing from the scope of the present invention. In the current example, the outer tubular member 603 may include an outer diameter of about 0.080 in, or in the range of about 0.060 in to about 0.090 in. A radial wall thickness of the outer tubular member 603, with respect to at least the segments 662, 663, 664, 665, may be about 0.005 in, or in the range of about 0.004 in to about 0.006 in. A radial clearance present between the inner diameter of the outer tubular member 603 and the outer diameter of the inner tubular member 511 may be about 0.003 in, or in the range of about 0.002 in to about 0.004 in. A radial wall thickness of the inner tubular member 511, with respect to at least the segments 562, 563, 564, 565, may be about 0.005 in, or in the range of about 0.004 in to about 0.006 in. A radial clearance present between the inner diameter of the inner tubular member 511 and the outer diameter of the fixed tubular segment 501 may be about 0.003 in, or in the range of about 0.002 in to about 0.004 in. A radial wall thickness of the fixed tubular segment 501 may be about 0.003 in, or in the range of about 0.002 in to about 0.004 in.

As mentioned above, each of the segments 562, 563, 564, 565 may include substantially the same inner diameter, outer diameter, and resulting wall thickness with respect to the inner tubular member 511, while each of the segments 662, 663, 664, 665 may similarly include substantially the same inner diameter, outer diameter, and resulting wall thickness with respect to the outer tubular member 603, thereby facilitating the butt joints formed at the intersections of these segments. However, in contrast, the first segment 561 of the inner tubular member 511 may include a different radial wall thickness in comparison to the adjacent disposed second segment 562 thereof, while the first segment 661 of the outer tubular member 603 may similarly include a different radial wall thickness in comparison to the adjacent disposed second segment 662 thereof. The differing wall thickness may result in each of the first segments 561, 661 having substantially the same inner diameter as each of the respective second segments 562, 662, but with each of the first segments 561, 661 having a reduced outer diameter in comparison to each of the respective second segments 562, 662. The radial thickness of each of the first segments 561, 661, which have been described as polyimide tubes, may be within the range of about 0.001 in to about 0.003 in, as opposed to the 0.005 in that may be utilized for each of the exemplary second segments 562, 662. Specifically, each of the second segments 562, 662 may be selected to include a radial wall thickness that is 1.5 to 5 times greater than that of each of the respective first segments 561, 661.

As shown in FIGS. 17-20, the reduced wall thickness of each of the first segments 561, 661 relative to each of the corresponding second segments 562, 662 results in the ability to form a lap joint as a result of the additional thickness of material able to flow over the first segments 561, 661 during a heat joining process. Each of FIGS. 17-20 includes the tubular components thereof labeled with respect to each of the inner tubular member 511 and the outer tubular member 603 due to the same process being utilized in forming each respective lap joint.

Figure 17:
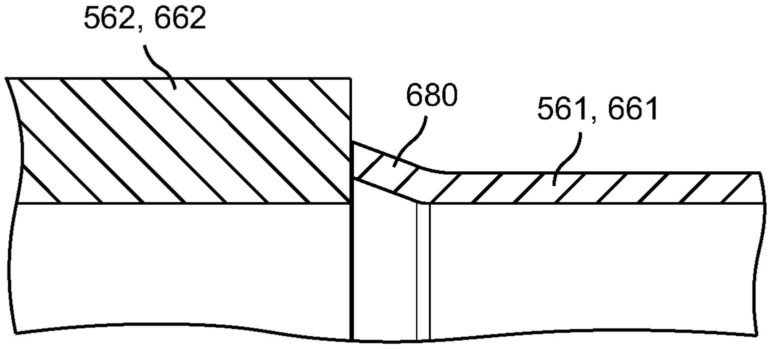
FIG. 17 is a fragmentary cross-sectional view showing a first tubular segment adjacent a second tubular segment prior to a joining thereof
Figure 18:
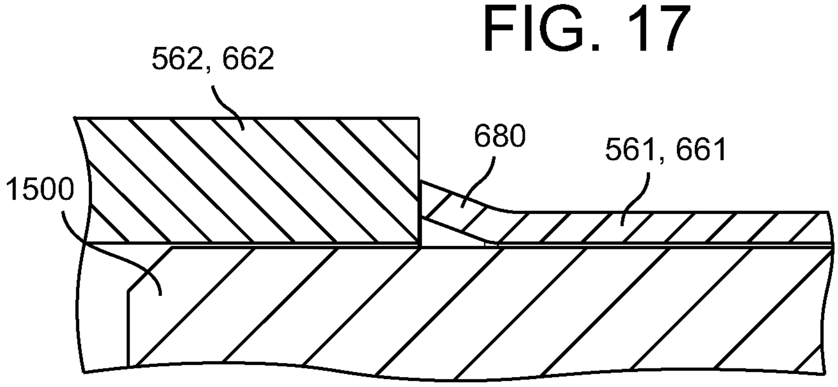
FIG. 18 is a fragmentary cross-sectional view showing a mandrel received within an interior of the first and second tubular segments.

As shown in FIG. 17, a distal end portion 680 of the first segment 561, 661 is deformed to be flared radially outwardly to cause an inner surface of the first segment 561, 661 to taper radially outwardly towards the distal direction. Alternatively, the inner surface of the first segment 561, 661 may be chamfered or otherwise tapered in the same manner, absent the disclosed flaring, while achieving a similar effect. The first segment 561, 661 is brought into abutment with a proximal end of the second segment 562, 662, which includes the increased radial wall thickness relative to the first segment 561, 661, while also having a substantially similar or identical inner diameter. The radial outward flaring of the first segment 561, 661 causes the distal end portion 680 to contact the proximal end of the second segment 562, 662 at a position spaced apart radially from each of an inner surface and an outer surface of the second segment 562, 662. As shown in FIG. 18, a mandrel 1500 is extended into the interior of each of the first segment 561, 661 and the second segment 562, 662 with a clearance present between an outer surface of the mandrel 1500 and the inner surface of each of the corresponding segment pairs 561, 562, 661, 662 being minimized.

Figure 19:
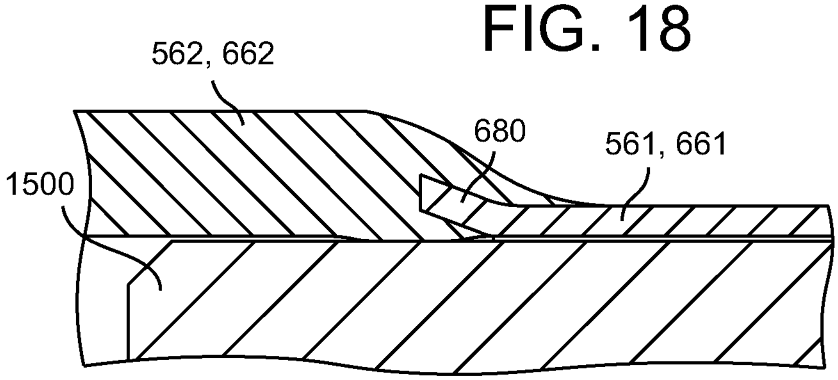
FIG. 19 shows a flow of the second tubular segment relative to the first tubular segment during a heat joining process.
Figure 20:
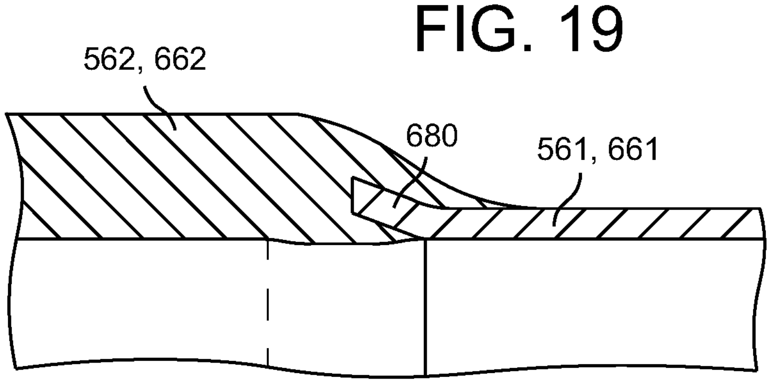
FIG. 20 shows a final configuration of a lap joint formed between the first and second segments following the removal of the mandrel.

Next, as can be seen by comparison of FIG. 18 to FIG. 19, a heat joining process is utilized where the segments 561, 562, 661, 662 abut each other to cause the thermoplastic polyamide polymer forming the second segment 562, 662 to melt and flow both radially outwardly of (over) and radially inwardly of (under) the distal end portion 680 of the first segment 561, 661. The heat joining process may include the placement of a heat bonding jacket, such as Teflon sleeve or a FEP shrink tube, over the joint where it is desired to heat and flow the second segment 562, 662. Next, heat is applied to cause the desired portion of the second segment 562, 662 to melt and flow. The first segment 561, 661 is formed from a thermoset polymer polyimide that will not melt and flow during the heat joining process. The mandrel 1500 forms a delimiting surface in the radial inward direction for delimiting the radially inward flow of the melted portions of the second segment 562, 662. Once the second segment 562, 662 has flowed sufficiently, the heat bonding jacket may be removed from over the joint and the mandrel 1500 may be retracted from within the segments 561, 562, 661, 662, thereby resulting in the lap joint of FIG. 20.

The use of the mandrel 1500 ensures that the portion of the second segment 562, 662 flowing along the outer surface of the mandrel 1500 will form a continuous surface with the inner surface of the first segment 561, 661 to prevent the formation of a ledge or bump therein that could ensnare a device or tubular member passing by the joint between the segments 561, 562, 661, 662. The flowing portion of the second segment 562, 662 flowing to contact both an inner surface and an opposing outer surface of the distal end portion 680 of the first segment 561, 661 significantly lengthens the contact area between the joining segments 561, 562, 661, 662, thereby providing a robust joint between the differing polymers forming the different segments 561, 562, 661, 662. The radial flaring of the distal end portion 680 also aids in providing an axial interference pattern for further solidifying the bond between the segments 561, 562, 661, 662.

According to an embodiment of the present invention, the inner tubular member 511 or the outer tubular member 603 may be formed via the following process. First, an elongate mandrel (not shown) may be provided to correspond to an inner luminal space of either respective tubular member 511, 603. Next, the aforementioned PTFE liner may be provided as an axially extending sheath that is received over the mandrel and positioned to correspond to the inner surface of any subset of the corresponding segments 561, 562, 563, 564, 565 or segments 661, 662, 663, 664, 665 in need of the liner, which may include the liner spanning all or portions of all of the segments 561, 562, 563, 564, 565 or segments 661, 662, 663, 664, 665. The described reinforcing braid may then be woven into a corresponding selection of the segments 561, 562, 563, 564, 565 or segments 661, 662, 663, 664, 665, such as within the distal segments 563, 564, 565 or the distal segments 663, 664, 665. Next, the described overcoats formed from the polymeric materials, which may be provided independently of each other, may be slid over the braids and/or exposed liner. The previously described butt joints mentioned between adjacent segments may correspond to the butt joints formed where these different overcoat segments abut each other over the liner and/or braid. Each of the intersections of the different segments 561, 562, 563, 564, 565 or segments 661, 662, 663, 664, 665 may then be joined by placing over a heat bonding jacket over each respective joint and then performing a heat joining process at each jacket. The mandrel can then be withdrawn.

The disclosed construction of each of the inner tubular member 511 and the outer tubular member 603 advantageously facilitates an ease of sliding of the inner tubular member 511 along the range of motion defined between the stops 507, 509. The fixed tubular segment 501 of the catheter device 500 may be provided as a stainless steel tube, which provides a rigid, smooth, and low-friction sliding surface over which the inner surface of the first segment 561 of the inner tubular member 511 may slide when the stop element 503 is adjusted to move axially in a direction towards either of the stops 507, 509. The first segment 561 of the inner tubular member 511 is formed from a rigid, smooth, and low-friction tube of a polyimide, which further promotes smooth and easy sliding between the inner tubular member 511 and the fixed tubular member 603. The first segment 661 of the outer tubular member 603 is also formed from a rigid, smooth, and low-friction tube of polyimide, which similarly promotes smooth and easy sliding of the inner tubular member 511 relative to the surrounding outer tubular member 603.

The fixed tubular segment 501 and the first segment 661 of the outer tubular member 603 are also axially spaced from one another in a manner wherein the first segment 561 of the inner tubular member 511 is able to maintain the beneficial sliding configuration when adjusted towards either of the stops 507, 509 during extension or retraction of the inner tubular member 511. That is, when the inner tubular member 511 is fully retracted and the stop element 503 is abutting the proximal stop 507, the first segment 561 is primarily disposed around and overlapping axially with the fixed tubular segment 501. As the stop element 503 is adjusted towards the distal stop 509, the first segment 561 of the inner tubular member 511 transitions from being primarily overlapped axially with the fixed tubular segment 501 to being primarily overlapped axially with the first segment 661 of the outer tubular member 603. This transition from an inner disposed smooth surface to an outer disposed smooth surface along a range of motion of the inner tubular member 511 accordingly results in a substantially constant frictional force being applied to the inner tubular member 511 due to similar contact areas and frictional forces being present between the corresponding surfaces of the first segment 561 of the inner tubular member 511 and each of the fixed tubular segment 501 and the first segment 661 of the outer tubular member 603.

The relatively high bending stiffness and rigidity of the fixed tubular segment 501, the first segment 561 of the inner tubular member 511, and the first segment 661 of the outer tubular member 603 also aids the operator in adjusting the slider/stop element 503 while maintaining desired function of the catheter device 500. The slider/stop element 503 is coupled directly to the first segment 561 of the inner tubular member 511 such that any forces applied to the slider/stop element 503 may be carried through the inner tubular member 511 if a misalignment or deformation thereof were to occur. The increased strength and rigidity of the sliding components forming the telescoping feature 505 accordingly aids in maintaining the desired guidance of the inner tubular member 511 relative to each of the fixed tubular segment 501 and the outer tubular member 603.

Figure 21:
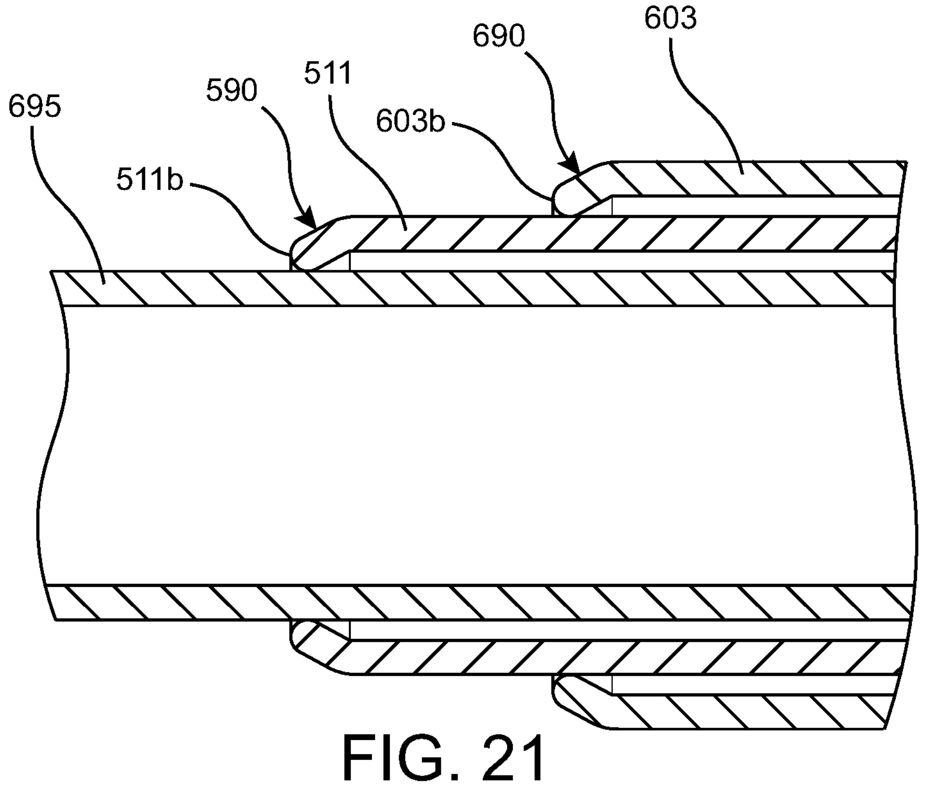
FIG. 21 is a fragmentary cross-sectional view showing a concentric arrangement of an inner-disposed cylindrical structure corresponding to a sheath or the like, the inner tubular member, and the outer tubular member.
Figure 22:
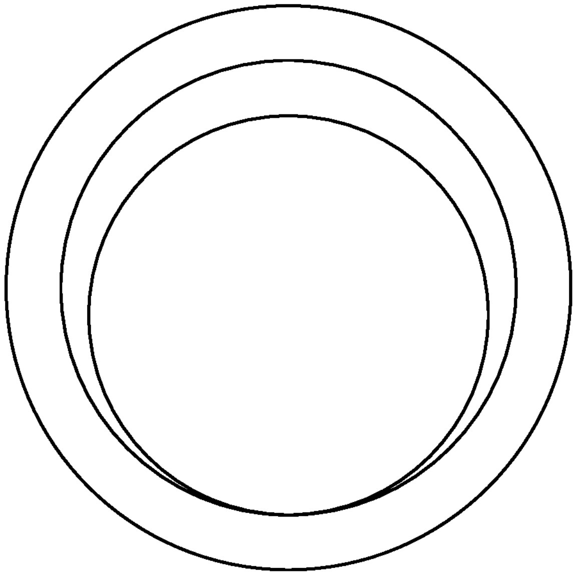
FIG. 22 shows an undesirable configuration between two cylindrical structures to be avoided by the configuration of the catheter device as shown in FIG. 21.

Referring now to FIG. 21, an additional safety feature of the catheter device 500 is disclosed according to an embodiment of the present invention. The safety feature shown in FIG. 21 is configured to avoid a circumstance such as that shown in FIG. 22, where an inner disposed cylindrical object is offset to one diametric side of an outer disposed cylindrical and thin-walled structure to form a crescent-shaped opening therebetween, such as may occur when a cylindrical device is extended through and past the distal end 511*b* of the inner tubular member 511 while axially misaligned, or when the cylindrical distal end 511*b* of the inner tubular member 511 is extended through the distal end 603*b* of the outer tubular member 603 while axially misaligned. The crescent-shaped opening may undesirably receive tissue therein when running along an interior of a surface such as a blood vessel due to the thin-walled outer cylindrical wall forming a cutting edge adjacent the opening. It is accordingly desirable to avoid an incidence of such a configuration at each of the distal ends 511*b*, 603*b* when the corresponding inner-received component is extended outwardly therefrom.

The embodiment of FIG. 21 shows the inner tubular member 511 as having a cylindrical structure 695 extending through an interior thereof, wherein the cylindrical structure 695 may be representative of any cylindrically shaped tool, device, sheath, conduit, or the like that may be associated with a procedure utilizing the inner luminal space of the catheter device 500 according to any of the processes described herein. The inner tubular member 511 includes an inwardly tapered distal end segment 590 directly at the distal end 511*b* thereof that contacts the outer surface of the cylindrical structure 695 around a circumference thereof while the remainder of the inner tubular member 511 disposed proximally from the distal end segment 590 is spaced apart radially from the outer surface of the cylindrical structure 695 to provide a radial clearance therebetween. The outer tubular member 603 similarly includes an inwardly tapered distal end segment 690 directly at the distal end 603*b* thereof that contacts the outer surface of the inner tubular member 511 around a circumference thereof while the remainder of the outer tubular member 603 disposed proximally from the distal end segment 690 is spaced apart radially from the outer surface of the inner tubular member 511 to provide a radial clearance therebetween. Each of the distal end segments 590, 690 is tapered to include a decreasing inner diameter at the corresponding distal end 511*b*, 603*b* while progressing in the distal direction of each of the tubular members 511, 603. This inward taper of the end segments 590, 690 results in each of the outer disposed tubular members 603, 511 gripping, contacting, or "hugging" the outer surface of the corresponding inner-disposed component 511, 695 around the circumference thereof when such inner-disposed components 511, 695 extend axially beyond the corresponding distal end 511*b*, 603*b*.

As mentioned above, the distal-most segment (about 1.5 mm) of each of the fifth segments 565, 665 forming the distal ends 511*b*, 603*b* may beneficially be provided devoid of reinforcement, lining, or the like to promote the greatest flexibility of each of the tubular members 511, 603 at the corresponding distal end 511*b*, 603*b* thereof. Each of the distal end segments 590, 690 may be formed by such a non-reinforced portion of the corresponding fifth segment 565, 665 (or equivalent if alternative configurations of segments are utilized) to promote the ability of each of the distal end segments 590, 690 to flex slightly in any radial direction to accommodate axial misalignment of the corresponding inner-disposed component 511, 695 while still maintaining a contact grip on the outer surface of the corresponding inner-disposed component 511, 695. The flexibility of each of the distal end segments 590, 690 may also be provided to prevent excessive friction where each of the distal end segments 590, 690 slides along the outer surface of the inner-disposed component 511, 695. Each of the distal end segments 590, 690 may be provided as an additional sixth segment joined to a distal end of the corresponding fifth segment 565, 665, as opposed to being an end portion of the corresponding fifth segment 565, 665. In any event, each of the distal end segments 590, 690 may be formed from a relatively soft and flexible polyamide polymer such as PEBAX 2533 or PEBAX 3533, as non-limiting examples.

Catheter devices described herein can be used in various ways. Among many available guide catheter shapes, the device operator can select one which he/she believes will result in adequate coaxial support for a successful intervention. The guide catheter can be used to engage the coronary artery in a standard fashion, as one would with any other type of guiding catheter that is currently available for use. For example, to engage the right coronary artery, one would take a standard 6Fr JR4 shape and advance the guide catheter to the ascending aorta with an 0.035 inch guidewire. Then, one would gently touch the aortic valve with the guide catheter then pull the guide catheter back with the right hand on the proximal portion, and subsequently, with the left (and right) hands apply a clockwise torque to turn the catheter into the right coronary artery to engage the ostium. Similarly, for the left coronary artery, one would take a standard shape guide catheter, such as a 6 Fr JL4 or EBU 4, and insert it over a 0.035 inch guidewire. The guide catheter and guidewire may be advanced in the ascending aorta, at which time the guidewire is removed. The guide catheter is advanced into the left coronary artery to engage the ostium.

For subsequent intervention, after the patient is adequately anticoagulated, an 0.014 inch wire is carefully advanced into the coronary artery to cross the stenotic lesion. Once the wire is past the lesion, one can advance balloon and stent catheters to treat the lesion. However, there may not be adequate support for the delivery of the balloon/stent catheter system. In this case, there are standard practices that can be employed such as: Use of a buddy wire system, further modification of the lesion with a balloon, use of a guide catheter extension, changing to a more supportive guidewire, changing to a larger guide catheter or a differently shaped guide catheter that may provide more support. These optional solutions are less than ideal, all requiring additional equipment, while disrupting the smooth workflow of an intervention. A better solution is needed, one that does not require the use of any additional equipment, which is important from a workflow, patient safety, and cost standpoint. An ideal solution would already be built into the guide catheter.

The method outlined below describes how the present technology can utilize a catheter device having a novel guide catheter system to provide improved treatment methods. The inner tubular member, in its initial configuration enters the body so its distal end does not protrude from the outer tubular member. The catheter device, in this initial configuration, is used to engage the coronary artery as described above. The lesion in question can be crossed with an 0.014 inch guidewire in a standard fashion as described above. When there is difficulty advancing the balloon/stent delivery system, or if it is anticipated that it may be difficult to advance, then the inner tubular member of the present technology can be extended into the vasculature to enhance guide catheter support.

The catheter device can be inserted into a vascular access site, into the femoral artery, near the groin using a technique well known for those in the art. Alternatively, the device may be inserted into the radial artery at the wrist of the patient. In both femoral or radial techniques, the catheter device is advanced through the vasculature until it reaches the ostium of a coronary artery. Markers on the catheter shaft can indicate the position of the catheter tip in the body and can consequently reduce the use of radiation in positioning the catheter.

Using the catheter device, an operator would first advance the balloon catheter about 10 to 15 mm into the coronary artery with his/her right hand, keeping the 0.014 inch guidewire in place with his/her left hand. The advanced balloon catheter may then serve as a rail to safely extend the inner tubular member of the catheter device. With the balloon catheter advanced in place down the treated vessel, then using the left hand, the inner guide catheter can be extended from the catheter device by manipulation of a control mechanism. The control mechanism acting on the inner tubular member, enabling both advancement into the artery or retraction into the outer tubular member, the means of actuation not utilizing space within the lumen of the inner tubular member thus enabling the use of the lumenal space for other purposes. This technique offers an extra measure of safety in preventing vessel dissection.

One method to extend the inner tubular member is for one to use his/her left hand to turn a small knob clockwise (for embodiment with rotating ring control mechanism), while holding the guidewire and balloon catheter with the right hand. Another method would be to extend the inner tubular member using a sliding mechanism with the left hand while holding the balloon and guidewire with the right hand.

Once the inner tubular member has been advanced into the coronary artery sufficient to provide support, then the intervention can be completed in typical fashion. To retract the extended inner tubular member when the intervention is complete, one would turn the knob counterclockwise or retract the sliding mechanism back using the left hand, depending on the embodiment. The other equipment used to perform the procedure would then be retracted and the access site closed to complete the procedure.

The embodiment of the catheter device 500 shown and described with reference to FIG. 21 may be beneficial in performing certain procedures wherein it is desirable to avoid the use of a cylindrical structure having an undesirably large outer diameter, such as a relatively larger bore sheath configured to receive a guide catheter then, in accessing certain arteries such as the relatively narrow radial artery (in comparison to the femoral artery). Instead, what may be referred to as a "railway" type system comprising a railway type dilator may be utilized in conjunction with the catheter device 500 in performing a procedure such as a radial PCI, among other similar or comparable procedures. The safety feature provided by the inclusion of the relatively flexible and radially inwardly tapered distal end segments 590, 690 at each of the distal ends 511*b*, 603*b* of the tubular members 511, 603 allows for such a procedure via the ability of the railway type dilator (corresponding to the cylindrical structure 695) and the inner tubular member 511 to safely extend past the corresponding distal ends 511*b*, 603*b* during use of the catheter device 500 absent the formation of the undesirable configuration shown in FIG. 22.

The radial PCI procedure may include the use of a needle and wire for gaining the radial access, which may also optionally include the use of a 5 Fr sheath. The catheter device 500 is adjusted to the extended position with the distal end 511*b* spaced apart distally from the distal end 603*b* and a portion of the inner tubular member 511 exposed. The railway type dilator is received into the inner luminal space of the catheter device 500. Radial access is then gained to the radial artery using the needle in a manner known according to the prior art. The 5 Fr sheath is then received in the radial artery, and through this 5 Fr sheath a 0.035 in wire is advanced into the ascending aorta. The 5 Fr sheath is then removed and the railway type dilator and surrounding catheter device 500 are advanced over the wire and into the ascending aorta. The railway type dilator is then removed from the wire, and the inner tubular member 511 is retracted. A Touhy fitting may be attached via the luer or hub 513 to facilitate flushing the inner luminal space with heparizined saline. The catheter device 500 is then utilized to engage the vessel and complete the procedure in accordance with the described methods of use of the catheter device 500.

As an alternative, the procedure may instead include the use of a 0.021 in wire for gaining the radial access, wherein this 0.021 in wire retracted through a port of the railway type dilator. The catheter device 500 may then be extended to the end of the previously extended railway formed by the railway type dilator immediately prior to removal of the railway. Next, the 0.035 in wire is advanced through the inner luminal space of the catheter device 500 prior to advancement of the inner tubular member 511 and completion of the procedure in accordance with the present disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A catheter device comprising:
a housing extending from a proximal end to a distal end;
a fixed tubular segment extending from a proximal end to a distal end, the proximal end of the fixed tubular segment immovably coupled to the housing adjacent the proximal end of the housing and the distal end of the fixed tubular segment disposed at a position adjacent the distal end of the housing, wherein the fixed tubular segment extends straight along its longitudinal axis between the proximal end and the distal end thereof;
an outer tubular member extending from a proximal end to a distal end, the proximal end of the outer tubular member immovably coupled to the housing adjacent the distal end of the housing;
an inner tubular member extending from a proximal end to a distal end, the inner tubular member slidably received within an interior of the outer tubular member and slidably received over an exterior of the fixed tubular segment, wherein the fixed tubular member is formed from a rigid and smooth metallic material to promote low-friction sliding of an interior of the inner tubular member over the exterior of the fixed tubular segment along a range of motion of the inner tubular member relative to the fixed tubular member, the inner tubular member configured to slide relative to each of the fixed tubular segment and the outer tubular member to selectively extend the distal end of the inner tubular member in a distal direction and/or to retract the distal end of the inner tubular member in a proximal direction, wherein each of the distal end of the inner tubular member and the distal end of the outer tubular member are always disposed distally relative to the distal end of the fixed tubular segment, wherein the inner tubular member is extendable to a position where the distal end of the inner tubular member is disposed distally relative to the distal end of the outer tubular member and wherein the inner tubular member is retractable to a position where the distal end of the inner tubular member is aligned with or disposed proximally relative to the distal end of the outer tubular member thereby allowing for either of the distal end of the inner tubular member or the distal end of the outer tubular member to form a distalmost surface of the catheter device.

2. The catheter device of claim 1, further comprising a slider immovably coupled to the inner tubular member, wherein the slider is configured to slide relative to the housing to cause the inner tubular member to slide relative to the fixed tubular segment and the outer tubular member.

3. The catheter device of claim 2, wherein the housing defines a proximal stop and a distal stop, wherein the slider is configured to slide between a retracted position wherein the slider abuts the proximal stop and an extended position wherein the slider abuts the distal stop.

4. The catheter device of claim 1, wherein a majority of a length of the fixed tubular segment is coextensive with the housing between the proximal end and the distal end thereof.

5. The catheter device of claim 1, wherein a length of a portion of the inner tubular member received around and co-extensive with the fixed tubular segment always decreases when the inner tubular member is slid in the distal direction.

6. The catheter device of claim 1, wherein a length of an inner luminal space formed by cooperation of an interior of the fixed tubular segment and an interior of the inner tubular member is increased when the inner tubular member is slid in the distal direction.

7. The catheter device of claim 1, wherein a first segment of the inner tubular member configured to slide over the fixed tubular segment includes the interior of the inner tubular member formed from a lining of polytetrafluoroethylene to provide a low-friction interface between the interior of the inner tubular member and the exterior of the fixed tubular segment.

8. The catheter device of claim 1, wherein the fixed tubular segment is a stainless steel tube.

9. The catheter device of claim 1, wherein the inner tubular member is formed from a plurality of segments, wherein the plurality of segments includes a first segment of the inner tubular member and a second segment of the inner tubular member, wherein the second segment of the inner tubular member is disposed towards the distal end of the inner tubular member relative to the first segment of the inner tubular member and wherein the second segment of the inner tubular member includes a lower bending stiffness than the first segment of the inner tubular member.

10. The catheter device of claim 9, wherein the plurality of segments further includes a third segment of the inner tubular member, wherein the third segment of the inner tubular member is disposed towards the distal end of the inner tubular member relative to the second segment of the inner tubular member and the third segment of the inner tubular member includes a lower bending stiffness than the second segment of the inner tubular member.

11. The catheter device of claim 9, wherein the outer tubular member is formed from a plurality of segments, wherein the plurality of segments includes a first segment of the outer tubular member and a second segment of the outer tubular member, wherein the second segment of the outer tubular member is disposed towards the distal end of the outer tubular member relative to the first segment of the outer tubular member and wherein the second segment of the outer tubular member includes a lower bending stiffness than the first segment of the outer tubular member.

12. The catheter device of claim 1, wherein the outer tubular member is shaped adjacent the distal end thereof and includes at least one curved segment.

13. The catheter device of claim 12, wherein, when a distal end portion of the inner tubular member is disposed within the outer tubular member, the distal end portion of the inner tubular member conforms to the at least one curved segment of the outer tubular member, and wherein, when the distal end portion of the inner tubular member extends distally beyond the distal end of the outer tubular member, the distal end portion of the inner tubular member assumes a straight configuration that is different from the at least one curved segment of the outer tubular member.

14. The catheter device of claim 1, wherein the outer tubular member changes in flexibility between the proximal end and the distal end thereof and wherein the inner tubular member changes in flexibility between the proximal end and the distal end thereof.

15. The catheter device of claim 1, wherein the distal end of the inner tubular member is formed at the end of a radially inwardly tapered segment of the inner tubular member.

16. The catheter device of claim 1, wherein the distal end of the outer tubular member is formed at the end of a radially inwardly tapered segment of the outer tubular member.

17. A catheter device comprising:

a housing extending from a proximal end to a distal end;

a fixed tubular segment extending from a proximal end to a distal end, the proximal end of the fixed tubular segment immovably coupled to the housing adjacent the proximal end of the housing and the distal end of the fixed tubular segment disposed at a position adjacent the distal end of the housing;

an outer tubular member extending from a proximal end to a distal end, the proximal end of the outer tubular member immovably coupled to the housing adjacent the distal end of the housing;

an inner tubular member extending from a proximal end to a distal end, the inner tubular member slidably received within an interior of the outer tubular member and slidably received over an exterior of the fixed tubular segment, the inner tubular member configured to slide relative to each of the fixed tubular segment and the outer tubular member to selectively extend the distal end of the inner tubular member in a distal direction and/or to retract the distal end of the inner tubular member in a proximal direction, wherein each of the distal end of the inner tubular member and the distal end of the outer tubular member are always disposed distally relative to the distal end of the fixed tubular segment, wherein the inner tubular member is extendable to a position where the distal end of the inner tubular member is disposed distally relative to the distal end of the outer tubular member and wherein the inner tubular member is retractable to a position where the distal end of the inner tubular member is aligned with or disposed proximally relative to the distal end of the outer tubular member thereby allowing for either of the distal end of the inner tubular member or the distal end of the outer tubular member to form a distalmost surface of the catheter device; and a flushing port formed through the housing and in fluid communication with a radial space defined between an exterior of the inner tubular member and the interior of the outer tubular member, the flushing port being configured to deliver a fluid to the radial space.

18. The catheter device of claim 17, further comprising a membrane disposed across the flushing port, the membrane being configured to permit fluid flow into the radial space and to resist fluid flow from the radial space back through the flushing port.

19. The catheter device of claim 17, further comprising a seal disposed between the housing and the inner tubular member, the seal configured to resist fluid flow between the housing and the inner tubular member in the proximal direction.

20. The catheter device of claim 19, wherein the seal comprises an O-ring disposed between the exterior of the inner tubular member and an interior of the housing.

* * * * *